(12) United States Patent
Bonda

(10) Patent No.: US 6,537,529 B1
(45) Date of Patent: Mar. 25, 2003

(54) SUNSCREEN COMPOSITIONS AND METHODS AND MATERIALS FOR PRODUCING THE SAME

(75) Inventor: Craig A. Bonda, Winfield, IL (US)

(73) Assignee: The C.P. Hall Company, Chicago, IL (US)

( * ) Notice: Subject to any disclaimer, the term of this patent is extended or adjusted under 35 U.S.C. 154(b) by 0 days.

(21) Appl. No.: 10/092,131

(22) Filed: Mar. 5, 2002

(51) Int. Cl.$^7$ .............................. A61K 7/42; A61K 7/44; A61K 7/00
(52) U.S. Cl. .............................. 424/59; 424/60; 424/40; 424/401
(58) Field of Search ........................ 424/59, 60, 400, 424/401

(56) References Cited

U.S. PATENT DOCUMENTS

| | | | |
|---|---|---|---|
| 4,387,089 A | 6/1983 | De Polo | 424/59 |
| 4,489,057 A | 12/1984 | Welters et al. | 424/47 |
| 4,562,067 A | 12/1985 | Hopp et al. | 424/59 |
| 5,882,633 A | 3/1999 | Pisson et al. | 424/59 |
| 5,972,324 A | 10/1999 | Zofchak et al. | 424/78.03 |

FOREIGN PATENT DOCUMENTS

WO   WO 00/44340   8/2000

OTHER PUBLICATIONS

Grunwald et al., "The Correlation of Solvolysis Rates," *J. Am. Chem. Soc.*, vol. 70, pp. 846–854 (1948).
Fainberg et al., "Correlation of Solvolysis Rates. III. t–Butyl Chloride in a Wide Range of Solvent Mixtures," *J. Am. Chem. Soc.*, vol. 78 pp. 2770–2777 (1956).
Kosower, "The Effect of Solvent on Spectra. I. A New Empirical Measure of Solvent Polarity Z–Values," *J. Am. Chem. Soc.*,vol. 80, pp. 3253–3260 (1958).
Dimroth et al., *Justus Liebigs Ann. Chem.*, vol. 661 pp. 1–37 (1963).
Beckwith, in "The chemistry of amides: Synthesis of amides," Zabicky, J., Ed. Intersience: New York, pp. 73–185 (1970).
Bentley et al., "Medium Effects on the Rates and Mechanisms of Solvolytic Reactions," *Adv. Phys. Org. Chem.*, vol. 14, pp. 1–67 (1977).
Haslem, "Recent Developments in Methods For the Esterification and Protection of the Carboxyl Group," *Tetrahedron*, vol. 36, pp. 2409–2433 (1980).
Kamlet et al., "An Examination of Linear Solvation Energy Relationships," *Progr. Phys. Org. Chem.*, vol. 13, pp. 485–630 (1981).
Bentley et al., "$Y_x$ Scales of Solvent Ionizing Power," *Progr. Phys. Org. Chem.*, vol. 17, pp. 121–158 (1990).
Turro, *Modern Molecular Photochemistry* Benjamin/Cummings Publ. Co., Menlo Park, California, pp. 296–361 (1991).
McNaught et al., "IUPAC Compendium of Chemical Terminology," $2^{nd}$ Ed. (1997).
Reichardt, "Solvents and Solvent Effects in Organic Chemistry," 2nd Ed., Chap. 7: Empirical Parameters of Solvent Polarity, VCH Publishers, New York, New York (1998).
Sayre et al., "Photostability Testing of Avobenzone," Allured's Cosmetics & Toiletries Magazine, vol. 114, No. 5, pp. 85–91 (May 1999).
Tarras–Wahlberg et al., "Changes in Ultraviolet Absorption of Sunscreens After Ultraviolet Radiation," *J. Investigative Dermatology*, vol. 113, No. 4, pp. 547–553 (1999).
"Photostabilty of HallStar Photostable SPF 32 Sunscreen Compared to Neutrogena UVA/UVB Sunblock SPF 30," Suncare Research Laboratories, Memphis, Tennessee (Oct. 5, 2000).

Primary Examiner—Shelley A. Dodson
(74) Attorney, Agent, or Firm—Marshall, Gerstein & Borun

(57) ABSTRACT

A method of preparing a sunscreen including a solvent system and a filter system, the method including the step of controlling the polarity of the solvent system to control the rate of photodecay of the filter system, as well as sunscreen compositions and compounds for producing sunscreen compositions, are disclosed.

14 Claims, 6 Drawing Sheets

SUNSCREEN COMPOSITIONS AND METHODS AND MATERIALS FOR PRODUCING THE SAME

BACKGROUND OF THE INVENTION

1. Field of the Invention

The field of the invention includes a photoactive coating composition and methods and materials for making a photoactive coating composition. More particularly, the field of the invention includes a sunscreen composition for use on human skin and methods and materials for formulating a sunscreen composition.

2. Brief Description of Related Technology

It is well known that ultraviolet radiation (light) having a wavelength from about 280 nm or 290 nm to about 320 nm (UV-B) is harmful to human skin, causing burns that are detrimental to the development of a good sun tan. UV-A radiation (about 320 nm to about 400 nm), while producing tanning of the skin, also can cause damage, particularly to very lightly-colored or sensitive skin, leading to reduction of skin elasticity and wrinkles. Therefore, a sunscreen composition for use on human skin preferably includes both a UV-A and a UV-B filter to prevent most of the sunlight within the full range of about 280 nm or 290 nm to about 400 nm from damaging human skin.

Ultraviolet radiation from the sun or artificial sources can also cause harm to coatings containing photoactive substances, such as photoactive pigments and dyes, by breaking down chemical bonds in the structure of a component such as a polymer, a pigment, or a dye. This photodegradation can lead to color fading, loss of gloss, and loss of physical and protective properties of a coating. Photodegradation can take place in several steps which include one or more components of a coating absorbing UV radiation. The absorbed radiation can excite the absorbing molecules and raise them to a higher energy level, which can be very reactive. If the molecule cannot be relaxed, bond cleavage and the formation of free radicals will occur. These free radicals can attack one or more color molecules and/or a polymer backbone and form more free radicals. UV-A and UV-B filters can also be used to absorb UV radiation to protect a pigmented coating.

The UV-B filters that are most widely used in the U.S. in commercial sunscreen compositions are paramethoxycinnamic acid esters, such as 2-ethylhexyl paramethoxycinnamate, commonly referred to as octyl methoxycinnamate or PARSOL MCX, octyl salicylate, and oxybenzone.

The organic UV-A filters most commonly used in commercial sunscreen compositions are the dibenzoylmethane derivatives, particularly 4-(1,1-dimethylethyl)-4'-methoxydibenzoylmethane (also called avobenzone, sold under the brand name PARSOL 1789). Other dibenzoylmethane derivatives described as UV-A filters are disclosed in U.S. Pat. Nos. 4,489,057; 4,387,089 and 4,562,067, the disclosures of which are hereby incorporated herein by reference. It is also well known that the above described UV-A filters, particularly the dibenzoylmethane derivatives, can suffer in rapid photochemical degradation, when used alone or when combined with the above-described most commercially used UV-B filters.

Typically, the above-described UV-B filters are combined with the above-described UV-A filters in a solution with other lipophilic or oily ingredients. This solution of oily ingredients, known to formulators of cosmetic products including sunscreens as the "oil phase," is typically, but not necessarily, dispersed with the help of emulsifiers and stabilizers into an aqueous solution composed primarily of water, to make an emulsion which becomes a final cream or lotion form of a sunscreen composition.

Sunscreen performance has been extremely difficult to predict based on the levels of sunscreen active compounds in the formulation, particularly when the formulation includes one or more sunscreen active compounds that suffer from relatively rapid photodegradation, such as avobenzone. Because of this, each formulation has required expensive laboratory testing to determine the UV absorbance, as a function of time (quantity) of exposure of the formulation to UV radiation.

The formulation of a final sunscreen composition has been achieved largely through an iterative trial-and-error process, based on known rules of thumb. A UV filter system (one or more UV-absorbing compounds) is selected to provide UV-A and/or UV-B protection. A solvent system is selected to dissolve the components of the UV filter system. Next, the concentrations of each component in the filter system dissolved in the solvent system are selected in an attempt to achieve a sunscreen having a particular sun protection factor (SPF). If the selected solvent system is not able to completely dissolve the UV filter system at the desired concentrations of UV filter components, then the solvent system must be changed. For example, a greater amount of one or more solvents can be used (effectively lowering the concentration of the UV filter system), or different solvents can be used in the solvent system. The formulated sunscreen composition is then tested in panels of human volunteers, e.g., according to a sunscreen monograph (see, e.g., Title 21 of the U.S. Code of Federal Regulations, Part 351) to measure the SPF of the composition.

In a SPF test, sunscreen compositions applied to the skin receive doses of UV energy simulating sun exposure. For example, for a product to be labeled as SPF 30 in the U.S., it must prevent sunburn until a UV dose equivalent to 30 times the minimal erythema dose (MED; 1 MED is about 21 mJoule/$cm^2$) is received. This dose is approximately equivalent to a full day of summer sun exposure.

If the sunscreen composition does not achieve the desired SPF, then the composition must be reformulated, typically by adding additional quantities of UV filters. Again, if the solvent system is not able to completely dissolve the UV filter system at the desired concentrations of UV filter components, then the solvent system must be changed again. The reformulated sunscreen composition containing a higher concentration of UV filters and, potentially, a different solvent system, is then re-tested to gauge SPF.

This iterative trial-and-error process is further complicated by the photodecay of the photoactive compounds in the sunscreen composition, such as UV filters. Sunscreen compositions containing rapidly-degrading photoactive compounds (e.g., avobenzone) degrade in rapid exponential fashion when exposed to UV radiation, but start out with SPF values several-fold higher than their values after dosing with UV radiation. Thus, the SPF rating after testing (e.g., after 30 MED) are the cumulative SPF values over the period of UV irradiation while one or more compounds may be degrading and losing effectiveness, further complicating the ability to formulate a sunscreen composition with a desired effectiveness.

SUMMARY

One aspect of the invention is a method of preparing a sunscreen composition including the step of controlling the polarity of a solvent system in the composition to control the rate of photodecay of a filter system in the composition.

Another aspect of the invention is a method of formulating a sunscreen composition, including the steps of selecting a filter system; preparing parallel mixtures of the filter system in a plurality of analytical solvent systems, all of the mixtures having substantially the same concentration of filter system; determining the polarity of each of the mixtures; determining a rate constant of photodecay of each of the mixtures, or sunscreen compositions including the mixtures; selecting a final solvent system based on its polarity; and mixing the filter system and the final solvent system.

Yet another aspect of the invention is a composition including a filter system and a solvent system, wherein a mixture of the filter system and the solvent system in the ratio present in the composition has a high polarity, for example, a composition having a high polarity may have a dielectric constant at least about 7.

Still another aspect of the invention is a sunscreen composition including a filter system and a solvent system, wherein the solvent system includes a amide containing a $C_4$–$C_{40}$ hydrocarbon.

Another aspect of the invention is sunscreen composition including a filter system and a solvent system, wherein the solvent system includes a diester of malic acid, wherein the malic acid is esterified with a $C_4$–$C_{30}$ hydrocarbon.

Yet another aspect of the invention is a sunscreen composition including a filter system and a solvent system, wherein the rate constant of photodecay of the filter system is about 200% or less of the theoretical minimum rate constant of photodecay.

Further aspects of the invention may become apparent to those skilled in the art from a review of the following detailed description, taken in conjunction with the appended claims. While the invention is susceptible of embodiments in various forms, described hereinafter are specific embodiments of the invention with the understanding that the disclosure is illustrative, and is not intended to limit the invention to the specific embodiments described herein.

DETAILED DESCRIPTION OF THE PREFERRED EMBODIMENTS

Figure 1:
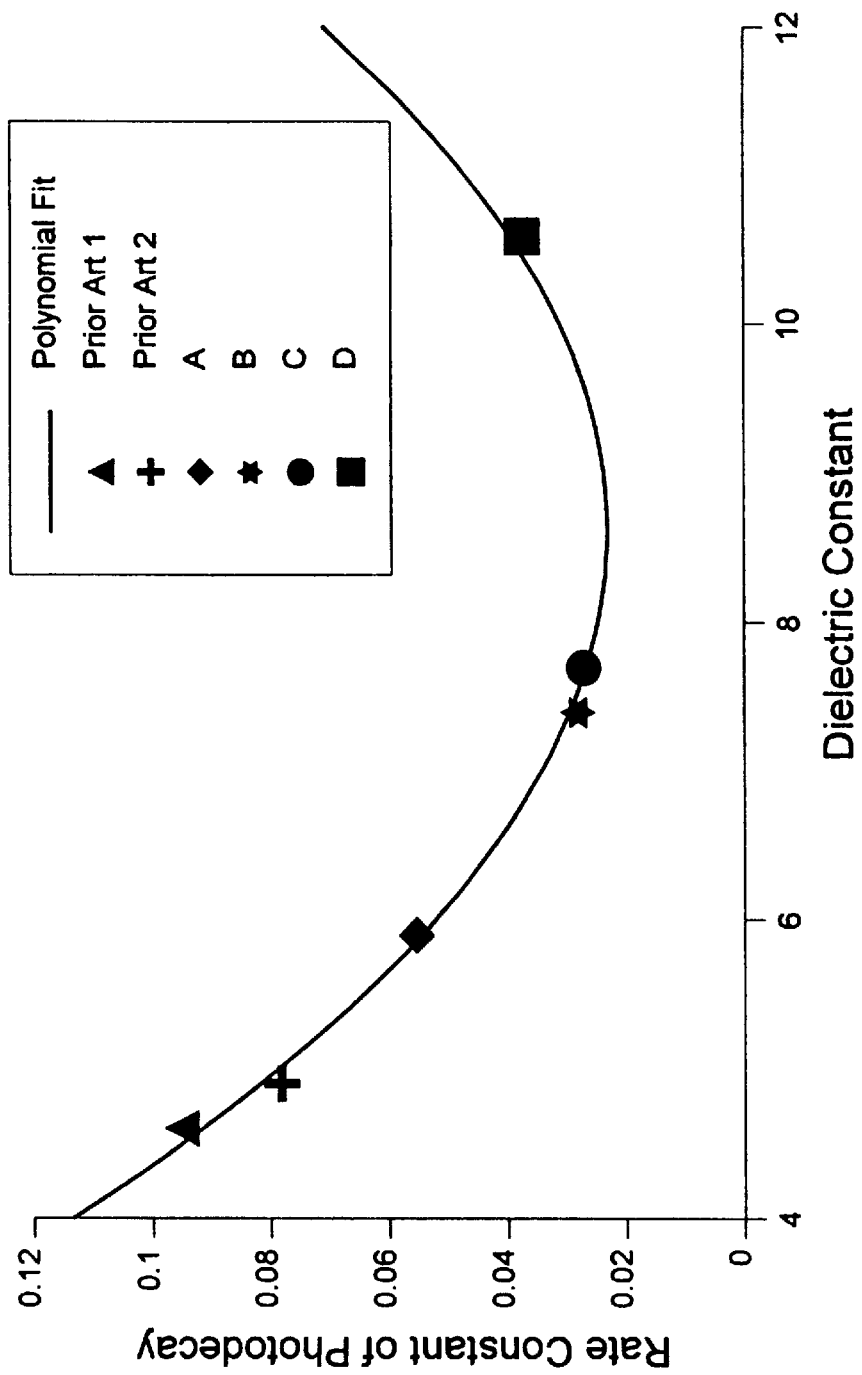
FIG. 1 is a plot of rate constant of photodecay versus dielectric constant for various sunscreen formulations. A curve for a second-order polynomial fit to the data is displayed for comparison.

Disclosed herein are sunscreen compositions and methods of making sunscreen compositions. It has been found that, quite surprisingly, the stability of a photoactive compound is affected by the polarity of a solution of the compound and, hence, in part based on the polarity of the solvent system. Now knowing that the polarity of the solution affects the stability, one might expect that the more polar the solution is, the greater the stability it will impart to the photoactive compound. In contrast, and even more surprisingly, it has been found (for example, with reference to a specific case) that as the polarity of a solvent system including a dissolved, rapidly-photodegradable compound is increased, the rate of photodecay initially decreases—but then increases again as the polarity is further increased. Thus, a photodegradable compound in solution will degrade as a second-order function of the overall polarity of the solution. Currently accepted photochemical theory provides the possibility that the mechanism by which a photodegradable compound is stabilized is the transfer of a photonically-excited electron to a nearby molecule of the same or different species (see, e.g., N. J. Turro, Modern Molecular Photochemistry, Chapter 9, Benjamin/Cummings Publ. Co., Menlo Park, Calif. (1991)), however photochemical theory does not describe the observed phenomena. Though not intending to be bound by such a belief, the observed phenomena are believed to coincide with the electron transfer theory of Professor Rudolph A. Marcus of the California Institute of Technology, for which he received the 1992 Nobel Prize in Chemistry.

The phenomena described above, coupled with the knowledge that, heretofore, sunscreen compositions have been formulated without specific regard to the relationship between polarity and photostability and, in newly-discovered fact, have had non-optimal polarities, forms the basis for at least one aspect of the methods and compositions described herein.

A photoactive compound is one that responds to light photoelectrically. In preferred compounds and methods disclosed herein, a photoactive compound is one that responds to UV radiation photoelectrically. For example, photoactive compounds that respond to UV radiation photoelectrically by rapid photodegradation can benefit highly from the compositions and methods disclosed herein, even though the benefits of the compositions and methods disclosed herein are not limited to such compounds. Photostability is a potential problem with all UV filters because they are deliberately selected as UV-absorbing molecules. In other applications, a photoactive compound may be a pigment or a dye (e.g., a hydrophobic dye).

UV filters include compounds selected from the following categories (with specific examples) including: p-aminobenzoic acid, its salts and its derivatives (ethyl, isobutyl, glyceryl esters; p-dimethylaminobenzoic acid); anthranilates (o-aminobenzoates; methyl, menthyl, phenyl, benzyl, phenylethyl, linalyl, terpinyl, and cyclohexenyl esters); salicylates (octyl, amyl, phenyl, benzyl, menthyl (homosalate), glyceryl, and dipropyleneglycol esters); cinnamic acid derivatives (menthyl and benzyl esters, alpha-phenyl cinnamonitrile; butyl cinnamoyl pyruvate); dihydroxycinnamic acid derivatives (umbelliferone, methylumbelliferone, methylaceto-umbelliferone); camphor derivatives (3-benzylidene, 4-methylbenzylidene, polyacrylamidomethyl benzylidene, benzalkonium methosulfate, benzylidene camphor sulfonic acid, and terephthalylidene dicamphor sulfonic acid); trihydroxycinnamic acid derivatives (esculetin, methylesculetin, daphnetin, and the glucosides, esculin and daphnin); hydrocarbons (diphenylbutadiene, stilbene); dibenzalacetone and benzalacetophenone; naptholsulfonates (sodium salts of 2-naphthol-3,6-disulfonic and of 2-naphthol-6,8-disulfonic acids); dihydroxy-naphthoic acid and its salts; o- and p-hydroxydiphenyldisulfonates; coumarin derivatives (7-hydroxy, 7-methyl, 3-phenyl); diazoles (2-acetyl-3-bromoindazole, phenyl benzoxazole, methyl naphthoxazole, various aryl benzothiazoles); quinine salts (bisulfate, sulfate, chloride, oleate, and tannate); quinoline derivatives (8-hydroxyquinoline salts, 2-phenylquinoline); hydroxy- or methoxy-substituted benzophenones; uric and vilouric acids; tannic acid and its derivatives; hydroquinone; benzophenones (oxybenzone, sulisobenzone, dioxybenzone, benzoresorcinol, 2,2',4,4'-tetrahydroxybenzophenone, 2,2'-dihydroxy-4,4'-dimethoxybenzophenone, octabenzone, 4-isopropyldibenzoylmethane, butylmethoxydibenzoylmethane, etocrylene, and 4-isopropyl-dibenzoylmethane).

Particularly useful are: 2-ethylhexyl p-methoxycinnamate, 4,4'-t-butyl methoxydibenzoylmethane, 2-hydroxy-4-methoxybenzophenone, octyldimethyl p-aminobenzoic acid, digalloyltrioleate, 2,2-dihydroxy-4-methoxybenzophenone, ethyl 4-[bis(hydroxypropyl)] aminobenzoate, 2-ethylhexyl-2-cyano-3,3-diphenylacrylate, 2-ethylhexylsalicylate, glycerol p-aminobenzoate, 3,3,5-trimethylcyclohexylsalicylate, methylanthranilate, p-dimethylaminobenzoic acid or aminobenzoate, 2-ethylhexyl p-dimethylaminobenzoate, 2-phenylbenzimidazole-5-sulfonic acid, 2-(p-dimethylaminophenyl-5-sulfoniobenzoxazoic acid and combinations thereof.

In one embodiment of the invention a photoactive compound is selected from the group consisting of UV-A filters and UV-B filters, and combinations thereof. In a cosmetically-acceptable sunscreen embodiment for use on human skin, a photoactive compound preferably is selected from approved (if regulated), cosmetically-acceptable UV-A filters, UV-B filters, and combinations thereof.

For example, for a product marketed in the United States, preferred cosmetically-acceptable photoactive compounds and concentrations (reported as a percentage by weight of the total cosmetic sunscreen composition) include: aminobenzoic acid (also called para-aminobenzoic acid and PABA; 15% or less), avobenzone (also called butyl methoxy dibenzoylmethane; 3% or less), cinoxate (also called 2-ethoxyethyl p-methoxycinnamate; 3% or less), dioxybenzone (also called benzophenone-8; 3% or less), homosalate (15% or less), menthyl anthranilate (also called menthyl 2-aminobenzoate; 5% or less), octocrylene (also called 2-ethylhexyl-2-cyano-3,3diphenylacrylate; 10% or less), octyl methoxycinnamate (7.5% or less), octyl salicylate (also called 2-ethylhexyl salicylate; 5% or less), oxybenzone (also called benzophenone-3; 6% or less), padimate O (also called octyl dimethyl PABA; 8% or less), phenylbenzimidazole sulfonic acid (water soluble; 4% or less), sulisobenzone (also called benzophenone-4; 10% or less), titanium dioxide (25% or less), trolamine salicylate (also called triethanolamine salicylate; 12% or less), and zinc oxide (25% or less).

Other preferred cosmetically-acceptable photoactive compounds and concentrations (percent by weight of the total cosmetic sunscreen composition) include diethanolamine methoxycinnamate (10% or less), ethyl-[bis (hydroxypropyl)]aminobenzoate (5% or less), glyceryl aminobenzoate (3% or less), 4-isopropyl dibenzoylmethane (5% or less), 4-methylbenzylidene camphor (6% or less), terephthalylidene dicamphor sulfonic acid (10% or less), and sulisobenzone (also called benzophenone-4, 10% or less).

For a product marketed in the European Union, preferred cosmetically-acceptable photoactive compounds and concentrations (reported as a percentage by weight of the total cosmetic sunscreen composition) include: PABA (5% or less), camphor benzalkonium methosulfate (6% or less), homosalate (10% or less), benzophenone-3 (10% or less), phenylbenzimidazole sulfonic acid (8% or less, expressed as acid), terephthalidene dicamphor sulfonic acid (10% or less, expressed as acid), butyl methoxydibenzoylmethane (5% or less), benzylidene camphor sulfonic acid (6% or less, expressed as acid), octocrylene (10% or less, expressed as acid), polyacrylamidomethyl benzylidene camphor (6% or less), ethylhexyl methoxycinnamate (10% or less), PEG-25 PABA (10% or less), isoamyl p-methoxycinnamate (10% or less), ethylhexyl triazone (5% or less), drometrizole trielloxane (15% or less), diethylhexyl butamido triazone (10% or less), 4-methylbenzylidene camphor (4% or less), 3-benzylidene camphor (2% or less), ethylhexyl salicylate (5% or less), ethylhexyl dimethyl PABA (8% or less), benzophenone-4 (5%, expressed as acid), methylene bisbenztriazolyl tetramethylbutylphenol (10% or less), disodium phenyl dibenzimidazole tetrasulfonate (10% or less, expressed as acid), bisethylhexyloxyphenol methoxyphenol triazine (10% or less), methylene bisbenzotriazolyl tetramethylbutylphenol (10% or less, also called TINOSORB M), and bisethylhexyloxyphenol methoxyphenyl triazine.(10% or less, also called TINOSORB S).

All of the above-described UV filters are commercially available. For example, suitable commercially-available organic UV filters are identified by trade name and supplier in Table 1 below

TABLE 1

| CTFA Name | Trade Name | Supplier |
|---|---|---|
| benzophenone-3 | UVINULM-40 | BASF Chemical Co. |
| benzophenone-4 | UVINUL MS-40 | BASF Chemical Co. |
| benzophenone-8 | SPECTRA-SORB UV-24 | American Cyanamid |
| DEA-methoxycinnamate | BERNEL HYDRO | Bernel Chemical |
| ethyl dihydroxypropyl-PABA | AMERSCREEN P | Amerchol Corp. |
| glyceryl PABA | NIPA G.M.P.A. | Nipa Labs. |
| homosalate | KEMESTER HMS | Humko Chemical |
| menthyl anthranilate | SUNAROME UVA | Felton Worldwide |
| octocrylene | UVINUL N-539 | BASF Chemical Co. |
| octyl dimethyl PABA | AMERSCOL | Amerchol Corp. |
| octyl methoxycinnamate | PARSOL MCX | Bernel Chemical |
| PABA | PABA | National Starch |
| 2-phenylbenzimidazole-5-sulphonic acid | EUSOLEX 6300 | EM Industries |
| TEA salicylate | SUNAROME W | Felton Worldwide |
| 2-(4-methylbenzildene)-camphor | EUSOLEX 6300 | EM Industries |
| benzophenone-1 | UVINUL 400 | BASF Chemical Co. |
| benzophenone-2 | UVINUL D-50 | BASF Chemical Co. |
| benzophenone-6 | UVINUL D-49 | BASF Chemical Co. |
| benzophenone-12 | UVINUL 408 | BASF Chemical Co. |
| 4-isopropyl dibenzoyl methane | EUSOLEX 8020 | EM Industries |
| butyl methoxy dibenzoyl methane | PARSOL 1789 | Givaudan Corp. |
| etocrylene | UVINUL N-35 | BASF Chemical Co. |
| methylene bisbenzotriazolyl | TINOSORB M | Ciba Specialty Chemicals |

TABLE 1-continued

| CTFA Name | Trade Name | Supplier |
| --- | --- | --- |
| tetramethylbutylphenol bisethylhexyloxyphenol methoxyphenyl triazine. | TINOSORB S | Ciba Specialty Chemicals |

A filter system is a set of one or more photoactive compounds. For example, a filter system for full-spectrum cosmetic sunscreen composition can consist of octyl methoxycinnamate and avobenzone. Another suitable filter system can consist of octyl salicylate, benzophenone-3, and avobenzone.

A solvent system includes one or more solvent compounds used to dissolve a filter system. As used herein, a solvent system is the set of all solvent compound(s) used to dissolve a filter system. Preferably, a solvent system for cosmetic sunscreen compositions will include and/or consist essentially of lipophilic organic chemicals. When a UV filter compound is water-soluble (e.g., phenylbenzimidazole sulfonic acid), however, the solvent system can include and/or consist essentially of a hydrophilic chemical.

Preferred solvent compounds include compounds that solubilize one or more components of a filter system. Suitable solvent compounds include, but are not limited to, $C_{12}$–$C_{15}$ alkyl benzoates, capric triglycerides, caprylic triglycerides, diethylhexyl adipate, diethylhexyl malate, diethylhexyl 2,6-naphthalate, ethylhexyl palmitate, ethylhexyl stearate, isoeicosane, isopropyl myristate, isopropyl palmitate, mineral oil, octyldodecyl neopentanoate, polyisobutene, and PPG-2 myristyl ether propionate. When used with UV filters, such as those identified above, preferred solvent compounds include solvents having even greater polarity, such as higher dielectric constants, for example. Thus, when used with UV filters, such as those identified above, solvent compounds preferably are selected from the amides, bis-urethanes, and malates described below, such as bis-(2-ethylhexyl) malate, bis-(2-butyloctyl) malate, isododecyl alcohol dimer with isopherone diisocyanate (IPDI), hexamethylene bis-(2-butyloctyl)urethane, hexamethylene bis-(2-ethylhexyl)urethane, N,N-dimethyldecanamide, and N,N-dipropylisosteramide.

In one embodiment, a preferred solvent compound has a dielectric constant of at least about 6, preferably about 7.5 to about 12. In another embodiment, a solvent compound in admixture with a filter set preferably will result in a dielectric constant of the mixture at least about 7, for example about 7 to about 12. In still another embodiment, a solvent system in admixture with a filter set preferably will result in a dielectric constant of the mixture at least about 8, for example about 8 to about 10.

The dielectric constant of a solvent system is a preferred measure of polarity of a solvent system, for example because the dielectric constant is a measure of both inherent and inducible dipole moments. Other measures of polarity include, but are not limited to, the induced and/or inherent (permanent) dipole moment (e.g., in Debye units), the Dimroth-Reichardt $E_T$ parameter (see, e.g., McNaught et al., Eds., IUPAC Compendium of Chemical Terminology, 2nd. Ed. (1997) and K. Dimroth et al., Justus Liebigs Ann. Chem., vol. 661, p. 1–37 (1963) (German)), ionizing power (see, e.g., T. W. Bentley et al., Adv. Phys. Org. Chem., vol. 14, p. 1–67 (1977); T. W. Bentley et al., Progr. Phys. Org. Chem., vol. 17, p. 121–158 (1990); see also the Grunwald-Winstein equation in E. Grunwald et al., J. Am. Chem. Soc., vol. 70, p. 846–854 (1948) and A. H. Fainberg et al., J. Am. Chem. Soc., vol. 78, p. 2770–2777 (1956), for example), Kamlet-Taft solvent parameters (see, e.g., M. J. Kamlet et al., Progr. Phys. Org. Chem. vol. 13, p. 485–630 (1981)), and the Z-value (see, e.g., E.M. Kosower, J. Am. Chem. Soc., vol. 80, p. 3253–3260 (1958)). See generally, C. Reichardt, "Solvents and Solvent Effects in Organic Chemistry" 2nd ed., Chap. 7: Empirical Parameters of Solvent Polarity, VCH Publishers, New York, N.Y., (1988).

Mathematically, photodegradation can be described by an exponential function. Thus, Q(a), the absorbance after a radiation dose (i.e., exposure to a quantity of radiation), can be described by the general equation (i), $$Q(a)=Ae^{-kr} \qquad (i)$$

wherein A is the original (pre-exposure) absorbance, e is the natural logarithm base, k is the rate constant of the photodecay, and r is the cumulative dose (e.g., in MED units). Because the absorbance decreases as the cumulative dose increases (photodecay), the overall term –k will be negative, and the greater the value of –k (i.e., closer to zero) and, thus, the lower the rate constant of photodecay, the lower is the rate of photodecay. For example, when Q(a) is plotted on a log scale versus r on a linear scale, the function forms a straight line with a slope equal to –k.

Furthermore, it has been found that, for a filter set that includes a photodegradable compound, the rate constant of photodecay of the filter set can be described as a second-order function of the polarity, preferably the dielectric constant (i.e., relative permittivity) of the filter set dissolved in the solvent system. Thus, for example, the rate constant of photodecay of a filter set can be described by the general equation (ii), $$k=-(x\in^2+y\in+z) \qquad (ii)$$

wherein x, y, and z can be empirically determined. The dielectric constant at the theoretical minimum rate constant of photodecay $\in_{k_{min}}$ described by formula (iii), $$\in_{k_{min}} = \frac{-y}{2x} \qquad (iii)$$

wherein x and y are defined as above.

Thus, according to one embodiment of the invention, a method of formulating a sunscreen composition includes the steps of: (a) selecting a filter system including a photoactive compound; (b) selecting a plurality of analytical solvent systems for the filter system; (c) preparing parallel mixtures of the filter system in the plurality of analytical solvent systems, all of the mixtures having substantially the same concentration of filter system; (d) determining the polarity of each of the mixtures; (e) determining a rate constant of photodecay of each of the mixtures at a selected wavelength; (f) selecting a final solvent system based on its polarity; and (g) mixing the filter system and the solvent system.

The method optionally includes the further step of preparing an emulsion from an aqueous system and the mixture of the filter system and the solvent system. When made, preferably, the emulsion is an oil-in-water emulsion.

Optionally, a method of formulating an emulsion sunscreen composition can include the steps of: (a) selecting a filter system including a photoactive compound; (b) selecting a plurality of analytical solvent systems for the filter system; (c) preparing parallel mixtures of the filter system in the plurality of analytical solvent systems, all of the mixtures having substantially the same concentration of filter system;

(d) determining the polarity of each of the mixtures; (e) selecting an aqueous system for the emulsion, (f) preparing parallel emulsions from the aqueous phase and the mixtures; (g) determining the rate constant of photodecay of each of the emulsions; (h) selecting a final solvent system based on its polarity; and (i) preparing an emulsion from the final solvent system, the filter system, the aqueous system. Alternatively, this method can be modified such that the polarity of each of the parallel emulsions is determined instead of, or in addition to, the parallel mixtures.

A photoactive compound preferably is selected from UV filters, such as those described above. For example, in a cosmetically-acceptable sunscreen composition, a photoactive compound is selected from cosmetically-acceptable UV filters. In one embodiment, the filter system includes a dibenzoylmethane derivative, preferably avobenzone. In the same or a different embodiment, the filter system preferably includes a paramethoxycinnamic acid ester.

The analytical solvent systems preferably include a lipophilic organic compound. The group of analytical solvent systems can be selected based on the overall polarity of each solvent system, as a result of the polarities of the individual components of the system. For example, the group of analytical solvent systems can be chosen to provide a range of polarities of the solvent systems in the group (e.g., by use of one or more of an amide, a bis-urethane, and a malate described below). When a group of analytical solvent systems is chosen to provide a broad range of polarities of the solvent systems (e.g., with dielectric constants ranging from about 4 to about 10, preferably from about 2 to about 12), then it can be easier to determine the relationship between the polarity and the rate constant of photodecay of the filter system. The group of analytical solvent systems can also be chosen to provide a range of polarities of the mixtures of the solvent systems with the filter system. The above-described selections can be based on the dielectric constant of each solvent component and/or the dielectric constant of each solvent system.

Selecting at least 3 analytical solvent systems allows for a the possibility of determining the particular function of rate constant of photodecay versus polarity. Preferably, at least 5 analytical solvent systems are selected, with varying degrees of polarity. Selecting more analytical solvent systems, with varying degrees of polarity, provides a better chance that rate constants of photodecay will be determined for polarities on both sides of the vertex (i.e., theoretical point of minimum rate constant of photodecay).

Next mixtures of the filter system in the plurality of analytical solvent systems are prepared, each mixture having substantially the same concentration of filter system in a solvent system. By preparing the mixtures such that each has substantially the same concentration of filter system (parallel mixtures), the subsequent determination of the rate constants of photodecay ensures that the effect of the solvent system on the rate constant of photodecay is isolated. Theoretically, both the concentration of filter system and the type of solvent system can be varied, with a consequence being that much more data would need to be accumulated, to estimate a third-order function (e.g., a three-dimensional surface having a parabolic cross-section), in order for such a method to have any predictive value.

According to the general methods described above, next the polarity is determined for either each of the mixtures, or parallel emulsions prepared from each of the mixtures with an aqueous system. As with the parallel mixtures described above, by preparing emulsions such that each has substantially the same type and concentration of aqueous system (parallel emulsions), the effect of the solvent system is isolated.

A step of determining the polarity of a mixture or an emulsion can be performed in various ways. For example, determining a polarity can include measuring a property that is a function of polarity, such as a dielectric constant. Measurement of a dielectric constant of a liquid can be performed by various sensors, such as immersion probes, flow-through probes, and cup-type probes, attached to various meters, such as those available from the Brookhaven Instruments Corporation of Holtsville, N.Y. (e.g., model BI-870) and the Scientifica Company of Princeton, N.J. (e.g., models 850 and 870). For consistency of comparison, preferably all measurements for a particular filter system are performed at substantially the same sample temperature, e.g., by use of a water bath. Generally, the measured dielectric constant of a substance will increase at lower temperatures and decrease at higher temperatures.

When a sunscreen composition produced according to a method disclosed herein includes other components, such as moisturizers, emollients, solvents, co-solvents, lubricants, thickeners, emulsifiers and other common cosmetic formulation additives, one or more of which would interfere with an apparatus for measuring polarity, then such a component is preferably omitted from the composition tested. Thus, for example, film-forming polymers or waxy solids such as those commonly used as emulsifiers, even if used in a final sunscreen formulation, preferably are omitted from the mixture of solvent system and filter system which is tested by an apparatus to determine its dielectric constant, to avoid fouling the dielectric probe. Conversely, other compositions that would not interfere with such measurements can be, and preferably are, added to the mixture of solvent system and filter system prior to measuring polarity.

Determining a polarity can also include retrieving a value of a property that is a function of polarity, such as a dielectric constant, from a reference document. A reference document is not limited to any particular type of document and can include, for example, journal articles, textbooks, electronic databases, and the like. A reference document can also include documentation of prior measurements, such as measurements made in practice of a method disclosed herein. As with measurements, for consistency of comparison, preferably all values retrieved for a particular filter system correspond to substantially the same sample temperature.

A step of determining the rate constant of photodecay of a mixture or an emulsion also can be performed in various ways. For example, determining a rate constant of photodecay at a selected wavelength can include the steps of measuring absorbance of the mixture of radiation at the selected wavelength before irradiation and after each of a plurality of exposures to radiation at the selected wavelength; and then calculating the rate constant based on the measurements. Absorbance before and after exposure to radiation can be measured by various methods, preferably by the method described in Example 1 below. Other methods are described, for example, in N. Tarras-Wahlberg et al., Changes in Ultraviolet Absorption of Sunscreens After Ultraviolet Radiation, J. Investigative Dermatology, Vol. 113, No. 4, p. 547–553 (October, 1999); R. M. Sayre, Photostability Testing of Avobenzone, Allured's Cosmetics & Toiletries magazine, Vol. 114, No. 5, p. 85–91 (May 1999); and "Photostability of HallStar Photostable SPF 32 Sunscreen Compared to Neutrogena UVA/UVB Sunblock SPF 30," distributed by Suncare Research Laboratories, Memphis, Tenn. (Oct. 5, 2000), the disclosures of which are hereby incorporated herein by reference.

Preferably, the selected wavelength is in the ultraviolet range. When the filter set includes a relatively rapidlyphotodecaying photoactive compound, then preferably the selected wavelength is in a range of wavelengths at which the photoactive compound absorbs radiation (e.g., within the peak range of absorbance).

Determining a rate constant of photodecay can also include retrieving a value of a rate constant of photodecay from a reference document.

The final solvent system can be selected based on its polarity, including based on a property that is a function of polarity, such as a dielectric constant. For example, if the lowest rate constant of photodecay of the mixtures or the emulsions described above is achieved with the use of a particular analytical solvent system (as would be expected), then that solvent system can be selected as the final solvent system for preparing the sunscreen composition.

By another option, a second-order function can be fit to the rate constants of photodecay for the parallel mixtures or emulsions (e.g., rate constant of photodecay as a function of polarity), and a solvent system can be selected based on that function. For example, a solvent system can be selected to provide a polarity of the filter system dissolved in the solvent system corresponding to the theoretical minimum rate constant of photodecay as predicted by the function. The function can predict a theoretical minimum rate constant of photodecay, but it may be the case that a range of polarities correspond to a practical minimum rate constant of photodecay.

Moreover, it is difficult to predict with accuracy the polarity of a mixture of two components, even knowing their individual polarities. Thus, when a filter system has a relatively high polarity, a final solvent system can be selected by selecting a final solvent system that has a polarity that is at least 80% of the polarity at the theoretical minimum rate constant of photodecay for the filter system. For example, the final solvent system can be selected to provide a dielectric constant that is at least 80% of the dielectric constant at the theoretical minimum rate constant of photodecay for the filter system. At least by rough approximation, the relatively high polarity of the filter system should contribute to the polarity of the mixed system to arrive at a system that has a polarity very close to the polarity at the theoretical minimum rate constant of photodecay for the filter system. Further refinement can be achieved through titration to a desired polarity value.

Thus, one method of method of preparing a sunscreen, the sunscreen including a solvent system and a filter system. and the filter system including a photoactive compound, includes the steps of controlling the polarity of the solvent system to control the rate of photodecay of the filter system (approximated, for example, by the rate constant of photodecay of the filter system). Optionally, the polarity of the solvent system can be controlled to minimize (e.g., about 150% or less of the theoretical minimum, preferably about 120% or less) the rate of photodecay of the filter system. Preferably, the dielectric constant of the solvent system is controlled to minimize the rate of photodecay of the filter system.

In similar fashion, a sunscreen composition is disclosed- herein, the sunscreen including a selected amount of filter system including a photoactive compound, and a selected amount of a solvent system including a lipophilic organic compound, wherein the polarity of a mixture of the filter system and the solvent system at a concentration determined by the ratio of the selected amounts corresponds to a minimum photodecay rate for the mixture. As with all methods and compositions disclosed herein, the rate of photodecay and any relative value thereof (e.g., a minimum.

rate of photodecay) can be approximated, for example, by the rate constant of photodecay of the filter system.

The practice of a method disclosed herein, and individual steps thereof, can be performed manually an/or with the aid of electronic equipment. Although processes have been described with reference to particular embodiments, a person of ordinary skill in the art will readily appreciate that other ways of performing the acts associated with the methods may be used. For example, the order of various of the steps may be changed without departing from the scope or spirit of the method. In addition, some of the individual steps can be combined, omitted, or further subdivided into additional steps.

A solvent system includes one or more solvent compounds used to dissolve a filter system. As used herein, a solvent system is the set of all solvent compound(s) used to dissolve a filter system. Preferred types of compounds used as solvents in a solvent system will be highly polar organic compounds that, in addition to contributing to dissolving a photoactive compound, will contribute to the overall polarity of the oil phase and/or a mixture of a filter system and a solvent system. For example, a preferred solvent will have a high dielectric constant relative to solvents commonly used in sunscreen compositions.

Preferred compounds suitable for use as solvents in a composition according to the disclosure include, but are not limited to, amides, malates, and bisurethanes, such as those described below.

As used herein, the term "alkyl" includes straight chained and branched hydrocarbon groups containing the indicated number of carbon atoms. typically methyl, ethyl, propyl, and butyl groups. The term "alkyl" also includes "bridged alkyl," eg., a $C_4$–$C_{16}$ bicyclic or polycyclic hydrocarbon group, for example, norbomyl, adamantyl, bicyclo[2.2.2] octyl, bicyclo[2.2.1]heptyl, bicyclo[3.2.1]octyl, or decahydronaphthyl. The term "cycloalkyl" is defined as a cyclic hydrocarbon group, e.g., cyclopropyl, cyclobutyl, cyclohexyl, and cyclopentyl.

As used herein, the term "alkenyl" is defined identically as "alkyl," except for containing a carbon-carbon double bond. The term "cycloalkenyl" is identical to "cycloalkyl" except containing a carbon-carbon double bond, e.g., cyclopropyl, cyclobutyl, cyclohexyl, and cyclopentyl.

As used herein, the term "aryl," alone or in combination, is defined herein as a monocyclic or polycyclic aromatic group, preferably a monocyclic or bicyclic aromatic group, e.g., phenyl or naphthyl.

A preferred amide suitable for use as a solvent in a sunscreen composition according to the disclosure has the structure of formula I,

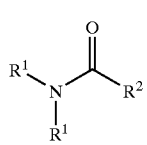

(I)

wherein $R^1$ is selected from the group consisting of $C_1$–$C_8$ alkyl and $R^2$ is selected from the group consisting of $C_3$–$C_{30}$ alkyl, $C_3$–$C_{30}$ alkenyl, aryl, and $C_3$–$C_8$ cycloalkyl. Preferably, the solvent is an amide of formula I, wherein $R^1$ is selected from the group consisting of $C_1$–$C_6$ alkyl and $R^2$ is selected from the group consisting of $C_5$–$C_{20}$ alkyl, and $C_5$–$C_{20}$ alkenyl. More preferably, the solvent is an amide of formula I, wherein $R^1$ is selected from the group consisting of $C_1$–$C_4$ alkyl and $R^2$ is selected from the group consisting of $C_8$–$C_{15}$ alkyl, and $C_8$–$C_{15}$ alkenyl. Most preferably, the solvent comprises a compound selected from the group consisting of N,N-dimethyldecanamide, N,N-diethyldecanamide, N,N-diisopropyldecanamide, N,N-dimethylisosteramide, N,N-diethylisosteramide, N,N-diisopropylisosteramide, N,N-dimethylmyristamide, N,N-diethylmyristamide, N,N-diisopropylmyristamide, and combinations thereof Preferred amides of formula I contribute to the solvation of a photoactive compound and an increase in the polarity of the mixture of a solvent system and a filter system. For example, the dielectric constant of a mixture of a solvent system and a filter system preferably is raised by the addition of an amide of formula I to the mixture.

Surprisingly, the compounds of formula Is particularly wherein $R^1$ is selected from the group consisting of $C_1$–$C_4$ alkyl and $R^2$ is selected from the group consisting of $C_5$–$C_{20}$ alkyl, exhibit much higher than expected solvency for crystalline UV filters. Examples of crystalline UV filters include oxybenzone, avobenzone, and octyl triazone (sold under the trade name UVINUL T-150 by BASF Corporation) and methylbenzilidene camphor. Indeed, compared to the traditional solvents used in sunscreen compositions, an amide for which results of solvency testing are shown in Table 2 below (N,N-dimethyldecanamide, CAS No. 14433-76-2, EINECS 238-405-1) proved to be far superior in its ability to solvate crystalline UV filters.

Some advantages of improved solvency include: (1) that less solvent can be used for the same level of one or more UV filters and/or (2) that a higher concentration of UV filter actives can be dissolved in the same volume of oil phase, translating into potential cost savings and better aesthetics.

Thus, other aspects of the invention include the use of an amide of structure I, e.g., N,N-dimethyldecanamide, as a solvent for a crystalline UV filter, such as oxybenzone, avobenzone, and octyl triazone, and a sunscreen composition that includes N,N-dimethyldecanamide and a crystalline UV filter. For example, one sunscreen embodiment can include a low concentration of N,N-dimethyldecanamide (relative to typical solvent concentrations) and a crystalline UV filter used in a typical concentration. Another sunscreen embodiment can include N,N-dimethyldecanamide (used at a typical solvent concentration) and a high concentration of a crystalline UV filter or combination of crystalline UV filters (relative to typical crystalline UV filter concentrations).

One embodiment of a sunscreen composition can include a solvent system including N,N-dimethyldecanamide and a filter system including avobenzone, wherein the concentration of avobenzone is greater than 28 wt. %, preferably greater than 30 wt. %, for example greater than 35 wt. %. Another embodiment can include a solvent system including N,N-dimethyldecanamide and a filter system including oxybenzone, wherein the concentration of oxybenzone is greater than 33 wt. %, preferably greater than 35 wt. %. Another embodiment can include a solvent system including N,N-dimethyldecanamide and a filter system including octyl triazone, wherein the concentration of octyl triazone is greater than 16 wt. %, preferably greater than 20 wt. %, for example greater than 30 wt. %.

TABLE 2

| Solvent | Solvency for Oxybenzone (wt. %) | Solvency for Avobenzone (wt. %) | Solvency for Octyl triazone (wt. %) |
| --- | --- | --- | --- |
| N,N-dimethyldecanamide | 38% | 37% | 37% |
| Octocrylene | 32% | 27% | 1% |
| Ethylhexyl methoxycinnamate | 24% | 17% | 15% |
| $C_{12}$–$C_{15}$ alkyl benzoates | 16% | 13.3% | 4% |
| Ethylhexyl salicylate | 18% | 16% | 5% |
| Diethylhexyl malate | 19% | 12.5% | 5% |
| Isopropyl myristate | 20% | 15% | <5% |
| Diethylhexyl malate | 15% | 15% | <5% |
| Diethylhexyl adipate | 20% | 10% | <5% |

The amides of formula I can be synthesized according to procedures that are commonly known in the art for the synthesis of amides. For example, a particularly simple procedure for amide synthesis involves the reaction of a primary or secondary amide with the acid halide of a carboxylic acid. See, Zabicky, *The Chemistry of Amides*, Wiley, New York, N.Y., p. 73–185 (1970).

Another preferred class of compounds suitable for use as solvents in the composition according to the disclosure include malates (esters of malic acid) of formula II,

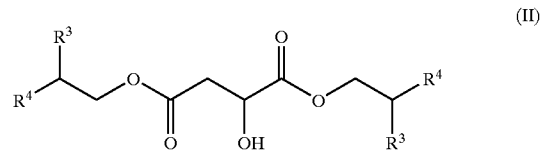

(II)

wherein, $R^3$ and $R^4$, independently, are selected from the group consisting of hydrogen, $C_1$–$C_{20}$ alkyl, $C_1$–$C_{20}$ alkenyl, aryl, and $C_3$–$C_8$ cycloalkyl. More preferably, a malate is a compound of formula I, wherein $R^3$ and $R^4$, independently, are selected from the group consisting of $C_1$–$C_{10}$ alkyl, and $C_1$–$C_{10}$ alkenyl. Most preferably, the solvent comprises a compound selected from the group consisting of dibutyloctyl malate, diisoamyl malate, and combinations thereof Preferred malates of formula II contribute to the solvation of a photoactive compound and an increase in the polarity of the mixture of a solvent system and a filter system. For example, the dielectric constant of a mixture of a solvent system and a filter system preferably is raised by the addition of a malate of formula II to the mixture.

The malates described above can synthesized by techniques that are commonly known in the art for esterification of acids. For example, the esterification of a carboxylic acid with an alcohol can be accomplished under both acid- and base-catalyzed conditions. See, Haslem, *Tetrahedron*, 36, p. 2409–2433 (1980).

A preferred bisurethane suitable for use as a solvent in a composition according to the disclosure has the structure of formula III,

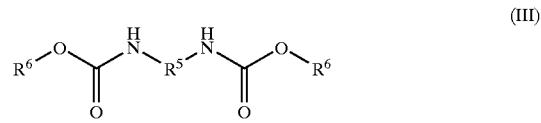

(III)

wherein $R^5$ and $R^6$, independently, are selected from the group consisting of $C_3$–$C_{30}$ alkyl, $C_3$–$C_{30}$ alkenyl, aryl, $C_3$–$C_8$ cycloalkyl, and $C_3$–$C_8$ cycloalkenyl. More preferably, a bisurethane will have formula III, wherein $R^5$ is selected from the group consisting of $C_3$–$C_{20}$ alkyl, $C_3$–$C_{20}$ alkenyl, aryl, C5–$C_6$ cycloalkyl and $C_5$–$C_6$ cycloalkenyl, and $R^6$ is selected from the group consisting of $C_3$–$C_{20}$ alkyl and $C_3$–$C_{20}$ alkenyl. For example, a preferred compound of formula III is selected from the group consisting of hexamethylene bis(2-butyloctyl)urethane, hexaamethylene bis(2-ethylhexyl)urethane, bis(dodecyl) isophorone urethane, bis(dodecyl) tetremethylxylyene urethane, 2,4-(2-butyloctyl)toluic urethane, 2,6-(2-butyloctyl)toluic urethane, 2,4-(dodecyl)toluic urethane, 2,6-(dodecyl)toluic urethane, bis(2-butyloctyl)-4,4'-biphenylene urethane, bis(2-butyloctyl)-2,4'-biphenylene urethane, bis(2-butyloctyl)-2,2'-biphenylene urethane, bis (dodecyl)-4,4'-biphenylene urethane, bis(dodecyl)-2,4'-biphenylene urethane, bis(dodecyl)-2,2'-biphenylene urethane, and combinations thereof. Preferred bisurethanes of formula III contribute to the solvation of a photoactive compound and an increase in the polarity of a mixture of a solvent system and a filter system. For example, the dielectric constant of a mixture of a solvent system and a filter system preferably is raised by the addition of a bisurethane of formula III to the mixture.

The bisurethanes described above can be synthesized by the reaction of a bisisocyanate with two equivalents of an alcohol, for example. A procedure for the synthesis of bisurethanes can be found in U.S. Pat. No. 5,972,324, the disclosure of which is hereby incorporated herein by reference.

In an embodiment wherein the sunscreen composition is an oil-in-water emulsion, a solvent system preferably is present in an amount from about 0.1% to about 40% by weight of the total weight of the composition More preferably, a solvent system of the compositions disclosed herein is present in an amount from about 3% to about 20% by weight of the total weight of the composition. However, in other embodiments, a composition can be produced as oily lotions, gels, solids sticks, aerosols, and other forms of cosmetic compositions. In such compositions there may only be a minimal aqueous phase, and the solvent system can make up almost the entire amount of the composition, for example up to about 95% or 99% by weight of the total weight of the composition.

A preferred UV-A filter for use as a photoactive compound in a filter system is selected from the group consisting of 2-hydroxy-4-methoxy benzophenone, avobenzone, 4-isopropyl dibenzoylmethane, other dibenzoylmethane derivatives, menthyl anthranilate, methylene bisbenzotriazolyl tetramethylbutylphenol, bisethylhexyloxyphenol meihoxyphenyl triazine, and combinations thereof. More preferably, a photoactive compound is selected from the group consisting of avobenzone, other dibenzoylmethane derivatives, and combinations thereof.

A preferred UV-B filter for use as a photoactive compound in a filter system is selected from the group consisting of 2-ethylhexyl p-methoxycinnamate, isoamyl p-methoxycinnamate, octyl salicylate, p-methylbenzylidene-D, L-camphor, sodium 2-phenylbenzimidazole-5-sulfonate, sodium 3,4-dimethylphenylglyoxylate, phenylbenzophenone, isooctyl 4-phenylbenzophenone-2'-carboxylate, p-methoxycinnamate, 2-phenyl-5-methylbenzoxazole, octyl p-dimethylaminobenzoate, p-aminobenzoic acid, 2-ethylhexyl p-dimethylaminobenzoate, pentyl p-dimethylaminobenzoate, ethyl 4-bis(hydroxypropyl)-aminobenzoate, 3,3,5-trimethylcyclohexyl salicylate, and combinations thereof. More preferably, a photoactive compound is selected from the group consisting of octyl salicylate, 2-ethylhexyl p-methoxycinnamate, and combinations thereof.

In a composition used on human skin to protect the skin from sunlight, a filter system preferably will include a combination of a UV-A and a UV-B filter. For example, the combination of avobenzone and octyl salicylate in a cosmetic sunscreen would typically rapidly photodegrade, but is stabilized in accordance with the compositions described herein (see, e.g., Example 2).

The compositions disclosed herein preferably include a filter system in an amount from about 1% to about 40% by weight of the total weight of the sunscreen composition. The compositions disclosed herein preferably include a filter system including a photoactive compound wherein a photoactive compound of the filter system can be present in an amount from about 0.1% to about 20% by weight of the total weight of the sunscreen composition. More preferably, a photoactive compound is present in the filter system in an amount from about 1% to about 15% by weight of the total weight of the sunscreen composition.

A preferred embodiment of the sunscreen composition includes a filter system including a photoactive compound dissolved in a solvent system that includes or consists essentially of a lipophilic organic compound, wherein a mixture of the filter system and the solvent system in the ratio present in the composition has a dielectric constant of at least about 8.

A preferred solvent system of this embodiment includes a malate of formula II described above. Another preferred solvent for this embodiment can be selected from amides of formula I described above. Most preferably, the solvent system of this embodiment includes a compound selected from the group consisting of N,N-dimethyldecanamide, N,N-diethyldecanamide, N,N-diisopropyldecanamide, N,N-dimethylisosteramide, N,N-diethylisosteramide, N,N-diisopropylisosteramide, N,N-dimethylmyristamide, N,N-diethylmyristamide, N,N-diisopropylmyristamide, and combinations thereof. An amide and/or malate can be combined with a bisurethane of formula III. Preferably, an amide and/or malate used as a solvent in the compositions disclosed herein is combined with a compound selected from the group consisting of hexamethylene bis(2-butyloctyl) urethane, hexamethylene bis(2-ethylhexyl)urethane, bis (dodecyl) isophorone urethane, bis(dodecyl) tetremethylxylyene urethane, 2,4-(2-butyloctyl)toluic urethane, 2,6-(2-butyloctyl)toluic urethane, 2,4-(dodecyl)toluic urethane, 2,6-(dodecyl)toluic urethane, bis(2-butyloctyl)-4,4'-biphenylene urethane, bis(2-butyloctyl)-2,4'-biphenylene urethane, bis(2-butyloctyl)-2,2'-biphenylene urethane, bis (dodecyl)-4,4'-biphenylene urethane, bis(dodecyl)-2,4'-biphenylene urethane, bis(dodecyl)-2,2'-biphenylene urethane, and combinations thereof.

Another embodiment of a sunscreen composition includes a filter system including a photoactive compound, and a solvent system including an amide of formula I. More preferably, the solvent system of the composition of this embodiment includes an amide selected from the group consisting of N,N-dimethyldecanamide, N,N-diethyldecanamide, N,N-diisopropyldecanamide, N,N-dimethylisosteramide, N,N-diethylisosteramide, N,N-diisopropylisosteramide, N,N-dimethylmyristamide, N,N-diethylmyristamide, N,N-diisopropylmyristamide, and combinations thereof.

Preferably, the solvent system of this embodiment of a sunscreen composition that includes an amide also includes a bisurethane of formula III. More preferably, the composition of this embodiment includes a bisurethane selected from the group consisting of hexamethylene bis(2-butyloctyl)urethane, hexamethylene bis(2-ethylhexyl) urethane, bis(dodecyl) isophorone urethane, bis(dodecyl) tetremethylxylyene urethane, 2,4-(2-butyloctyl)toluic urethane, 2,6-(2-butyloctyl)toluic urethane, 2,4-(dodecyl) toluic urethane, 2,6-(dodecyl)toluic urethane, bis(2-butyloctyl)-4,4'-biphenylene urethane, bis(2-butyloctyl)-2,4'-biphenylene urethane, bis(2-butyloctyl)-2,2'-biphenylene urethane, bis(dodecyl)-4,4'-biphenylene urethane, bis(dodecyl)-2,4'-biphenylene urethane, bis(dodecyl)-2,2'-biphenylene urethane, and combinations thereof. The solvent system of this embodiment can optionally can include a malate of formula II described above.

Another embodiment of a sunscreen composition includes a filter system including a photoactive compound and a solvent system including a compound selected from the group consisting of dibutyloctyl malate, diusoamyl malate, and combinations thereof.

The solvent system of this embodiment, optionally, can be supplemented with an amide of formula I. Preferably, the solvent system includes an amide selected from the group consisting of N,N-dimethyldecanamide, N,N-diethyldecanamide, N,N-diisopropyldecanamide, N,N-dimethylisosteramide, N,N-diethylisosteramide, N,N-diisopropylisosteramide, N,N-dimethylmyristamide, N,N-diethylmyristamide, N,N-diisopropylmyristamide, and combinations thereof.

Optionally, the solvent system of this embodiment that includes a malate can be supplemented with a bisurethane of formula III, described above. Preferably, the solvent system includes a bisurethane selected from the group consisting of hexamethylene bis(2-butyloctyl)urethane, hexamethylene bis(2-ethylhexyl)urethane, bis(dodecyl) isophorone urethane, bis(dodecyl) tetremethylxylyene urethane, 2,4-(2-butyloctyl)toluic urethane, 2,6-(2-butyloctyl)toluic urethane, 2,4-(dodecyl)toluic urethane, 2,6-(dodecyl)toluic urethane, bis(2-butyloctyl)-4,4'-biphenylene urethane, bis(2-butyloctyl)-2,4'-biphenylene urethane, bis(2-butyloctyl)-2,2'-biphenylene urethane, bis(dodecyl)-4,4'-biphenylene urethane, bis(dodecyl)-2,4'-biphenylene urethane, bis(dodecyl)-2,2'-biphenylene urethane, and combinations thereof.

Bis(2-butyloctyl) malate is a malate of formula II, wherein $R^3$ is n-butyl alkyl and $R^4$ is n-hexyl alkyl, and is designed to act as a solvent in a composition according to the disclosure. Thus, another embodiment is the compound shown in formula II, described as bis(2-butyloctyl)malate. Bis(2-butyloctyl) malate can synthesized by techniques that are commonly known in the art for the esterification of acids.

Another embodiment of a sunscreen composition includes a selected amount of a filter system including a photoactive compound, and a selected amount of a solvent system including a lipophilic organic compound, wherein the rate constant of photodecay of the filter system is about 150% or less, preferably about 120% or less, of the theoretical minimum photodecay rate constant for the filter system.

The solvent system and filter system of this embodiment can include a compound such as an amide of formula I, a malate of formula II, and a bisurethane of formula III. One or more of these solvents can contribute to the overall polarity of the composition, as taught herein, such that the photodecay rate of the filter system can be minimized to approach the theoretical minimum photodecay rate for that filter system.

A sunscreen composition according to this embodiment can also include a solvent commonly used in sunscreen compositions, including but not limited to, isoeicosane, polyisobutene, mineral oil, octyldodecyl neopentanoate, ethylhexyl stearate, ethylhexyl palmitate, isopropyl palmitate, isopropyl myristate, $C_{12}$–$C_{15}$ alkyl benzoates, caprylic triglyceride, capric triglyceride, and combinations thereof. Thus, an unoptimized sunscreen composition can be optimized by the reduction of the photodecay rate of the filter system, for example to about 150% or less of the theoretical minimum, by the addition of a highly polar solvent such as those described herein (see Examples 1–6 below).

Any one of the sunscreen compositions described herein can be combined with cosmetically acceptable emollients, stabilizers, emulsifiers, such as those known in the art, and combinations thereof. These additives can be used in preparing an emulsion from an aqueous system and the mixture of the filter system and the solvent system. When made, preferably the emulsion is an oil-in-water emulsion.

Any one of the sunscreen compositions described herein can include a solvent such as those commonly found in cosmetic sunscreen formulations, including but not limited to, a compound selected from the group consisting of isoeicosane, polyisobutene, mineral oil, octyldodecyl neopentanoate, ethylhexyl stearate, ethylhexyl palmitate, isopropyl palmitate, isopropyl myristate, $C_{12}$–$C_{15}$ alkyl benzoates, caprylic triglyceride, capric triglyceride, and combinations thereof.

A mixture of solvent system and filter system, in accordance with one preferred embodiment, are combined with well-known cosmetically-acceptable additives, such as moisturizers, emollients, solvents, co-solvents, lubricants, thickeners, emulsifiers and/or other common cosmetic formulation additives for solubility of sunscreen active compounds, emulsification, thickening and to provide other skin enhancement, e.g., moisturizing properties. The compositions can be produced as oily lotions, gels, solid sticks, emulsions, aerosols, and all other forms of cosmetic compositions. The dielectric constants of various sunscreen additive materials are well known, see, Dielectric Constant Reference Guide of ASI Instruments, Inc., pages 1–64, (http://asiinstruments.com/dc1.html), hereby incorporated herein by reference. The dielectric constants of some sunscreen ingredients at 25° C. are shown in Table 3 below.

TABLE 3

|  | Dielectric Constant at 25° C. |
| --- | --- |
| Isoeicosane (saturated hydrocarbon) | 2.04 |
| Polyisobutene (saturated hydrocarbon | 2.13 |
| Mineral oil | 2.13 |
| Octyldodecyl neopentanoate | 3.04 |
| Ethylhexyl stearate | 3.05 |
| Ethylhexyl palmitate | 3.06 |
| Isopropyl palmitate | 3.20 |
| Isopropyl myristate | 3.24 |
| $C_{12}$–$C_{15}$ alkyl benzoates | 3.78 |
| Caprylic/capric triglycerides | 3.83 |
| PPG-2 myristyl ether propionate | 3.88 |
| Diethylhexyl adipate | 4.21 |
| Diethylhexyl 2,6-naphthalate | 4.34 |
| Dibutyloctyl malate | 4.65 |
| Dioctyl malate | 4.74 |
| Diethylhexyl malate | 4.74 |
| Dioctyl malate | 5.78 |
| Diethylhexyl malate | 5.88 |
| Ethylhexyl methoxycinnamate | 5.98 |
| Ethylhexyl salicylate | 6.20 |
| Diisoamyl malate | 7.42 |
| Isododecyl alcohol dimer with IPDI | 10 (estimated.) |
| Isododecyl alcohol dimer with HDI | 10 (estimated.) |

TABLE 3-continued

| | Dielectric Constant at 25° C. |
|---|---|
| Avobenzone | 10 (estimated.) |
| Octocrylene | 11.08 |
| N,N-dimethyldecanamide | 12.43 |
| Benzophenone-3 | 13 |
| Water | 80 |

EXAMPLES

The following examples are provided to illustrate the invention but are not intended to limit the scope of the invention.

Example 1

A series of sunscreen compositions was produced according to the oil phase ingredients and concentrations (formulations) shown in Table 4 below.

TABLE 4

| | $\epsilon$ (25° C.) | Prior Art 1 | Prior Art 2 | A | B | C | D |
|---|---|---|---|---|---|---|---|
| | | Concentrations reported as wt. % of total formulation | | | | | |
| octyl salicylate | 6.2 | 5% | 5% | 5% | 5% | 5% | 5% |
| benzophenone-3 | 13† | 3% | 3% | 3% | 3% | 3% | 3% |
| avobenzone | 10* | 2% | 2% | 2% | 2% | 2% | 2% |
| saturated hydrocarbons | 2.04 to 2.13 | 5% | 5% | 5% | | | |
| isopropyl myristate | 3.24 | 10% | | | | | |
| $C_{12}$—$C_{15}$ alkyl benzoates | 3.78 | | 10% | | | | |
| diethylhexyl malate | 5.88 | | | 10% | 15% | 10% | 7.5% |
| isododecyl alcohol dimer w/IPDI | 10* | | | | | 5% | |
| N,N-dimethyldecanamide | 12.43 | | | | | | 7.5% |
| oil phase dielectric constant ($\epsilon$) | | 4.56 | 4.92 | 5.89 | 7.44 | 7.66 | 10.59 |
| photodecay rate constant (% of theoretical minimum) | | 0.1 (435%) | 0.078 (339%) | 0.04 (174%) | 0.029 (126%) | 0.028 (122%) | 0.038 (165%) |

*denotes estimated value
†denotes literature value

The formulations labeled "Prior Art 1" and "Prior Art 2" were formulated using typical prior art solvents, in typical concentrations. Formulations "A" though "D" were formulated according to the disclosure herein, and resulted in higher dielectric constants of the oil phases.

For each sunscreen composition, the filter system was blended with the solvent system to form an oil phase. Next, the dielectric constant of the oil phase was measured. Dielectric constant measurements were performed with a Scientifica model 850 dielectric constant meter.

Emulsions were created with each oil phase and an aqueous phase. The aqueous phase was identical for each emulsion. The resulting sunscreens were tested for photostability by measuring absorbance on a Labsphere UV-1000S Ultraviolet Transmittance Analyzer (software version 1.27) before and after irradiation with a Solar Light Company model 16S solar simulator (equipped with a WG 320 filter to transmit radiation greater than 290 nm) in 5 MED (105 mJ/cm$^2$) increments up to 25 to 35 MED cumulative dose. Output was monitored by a PMA 2105 UV-B DCS Detector (biologically weighted) and controlled by a PMA 2100 Automatic Dose Controller (Solar Light Co.).

A synthetic skin substrate was used for testing the sunscreen compositions (VITRO-SKIN substrate by IMS, Inc. of Milford, Conn.). To prepare the substrate, a 200 g solution of 30 wt. % glycerin. and 70 wt. % deionized water was added to an IMS hydrating chamber, and a sheet of VITRO-SKIN was placed in the hydrating chamber and left overnight (approx. 16 hours). Several 6.5 cm squares were cut from the hydrated VITRO-SKIN and used for absorbance measurements.

To prepare slides for testing, a minimum 100 μl of sunscreen composition is drawn or placed into a pipet tip (Justor 1100 DG, set to dispense 100 μl). Using steady, even pressure on the pipettor plunger, the test substance was applied to VITRO-SKIN square in a pattern of at least 50 small dots arranged to cover a 6 cm center of a square. The VITRO-SKIN square was then placed on a foam block, and the test material was spread by finger (covered with a latex glove or finger cot), first in a circular motion, then by a side-to-side motion during which the VITRO-SKIN is deformed by the pressure. The square was then mounted in a slide holder (60 mm×60 mm glassless slide mounts with metal masks by Gepe Management AG, Zug, Switzerland) and allowed to dry for 30–60 minutes.

To test stability, a slide was positioned on the UV transmittance analyzer using registration marks, and a scan of a 1 cm spot on the slide was performed. The slide was then transferred to a holder placed adjacent to the solar simulator and, using a calipers, was positioned such that the beam of UV radiation exiting the solar simulator illuminated the same 1 cm spot on the slide. The following software settings were used: UV-B—290–320 nm; UV-A—320–400 nm; SPF—290–400 nr; Spectral Irradiance; Noon, July 3, Albuquerque, N. Mex.; SPF Spectral Irradiance and Erythermal Effectiveness settings as set by manufacturer. Following an exposure of 5 MED, the slide was again placed in position on the UV transmittance analyzer, and a scan of the exposed spot was performed. The procedure was repeated on the same 1 cm spot on the slide until the desired total radiation dosage was achieved.

The absorbance versus cudmulative MED data at 370 nm (approximate peak absorbance for avobenzone) were fit to equation (i), described above, to calculate the rate constant of photodecay for each formulation.

FIG. 1 plots the rate constant of photodecay versus dielectric constant for each formulation described in Table 4 above. This Figure shows that as the dielectric constant of the oil phase was increased, the rate constant of photodecay approached a minimum and then, quite surprisingly, increased again.

The data were then fit to a second order polynomial having the form of general equation (ii)

$$k = -(x\epsilon^2 + y\epsilon + z) \quad \text{(ii)}$$

with the result that x=-0.004215, y=0.072748, and z=-0.33701. The polynomial provided a very good fit to the data (strong correlation), as evidenced by a coefficient of determination ($R^2$) of 0.9927. Thus, a definite, direct relationship exists between the polarity (dielectric constant) and the rate of photodecay of the filter system. The second-order polynomial curve is displayed on FIG. 1 for comparison. According to equation (iii) described above, the dielectric constant at the theoretical minimum rate constant of photodecay for this filter system is 8.63, and the theoretical minimum rate constant of photodecay (via Formula ii) is 0.023.

Example 2

To test the predictive value of a method of formulating a sunscreen composition disclosed herein, two additional sunscreen compositions were produced using the same filter system as in Example 1, and parallel dielectric constant and rate constant of photodecay measurements were made. Subsequently, the two new formulations and formulation "C" from Example 1 above were sent to an independent laboratory for SPF testing of each formulation performed on five human subjects. The sunscreen compositions were produced according to the oil phase ingredients and concentrations (formulations) shown in Table 5. below. Dielectric constants and rate constants of photodecay were measured as described in Example 1, and resulted in the values reported in Table 5 below. Formula C from Example 1 is reproduced for convenience of comparison.

TABLE 5

|  | $\epsilon$ | Prior Art 3 | C | E |
| --- | --- | --- | --- | --- |
|  |  | Concentrations reported as wt. % of total formulation | | |
| octyl salicylate | 6.2 | 5% | 5% | 5% |
| benzophenone-3 | 13† | 3% | 3% | 3% |
| avobenzone | 10* | 2% | 2% | 2% |
| $C_{12}$–$C_{15}$ alkyl benzoates | 3.78 | 10% | | |
| octyldodecyl neopentanoate | 3.04 | 5% | | |
| diethylhexyl malate | 5.88 | | 10% | |
| isododecyl alcohol dimer w/IPDI | 10* | | 5% | |
| diisoamyl malate | 7.42 | | | 10% |
| dibutyloctyl malate | 4.65 | | | 5% |
| oil phase dielectric constant ($\epsilon$) | | 5.48 | 7.66 | 7.83 |
| photodecay rate constant (% of theoretical minimum) | | 0.0621 (269%) | 0.0275 (119%) | 0.02367 (102%) |
| Average SPF (% increase over prior art) | | 17.14 | 20.6 (+20%) | 21.3 (+24%) |

*denotes estimated value

The formulation labeled "Prior Art 3" was formulated using typical prior art solvents, in typical concentrations. Formulations "C" and "E" were formulated according to the disclosure herein, and resulted in higher dielectric constants of the oil phases.

Figure 2:
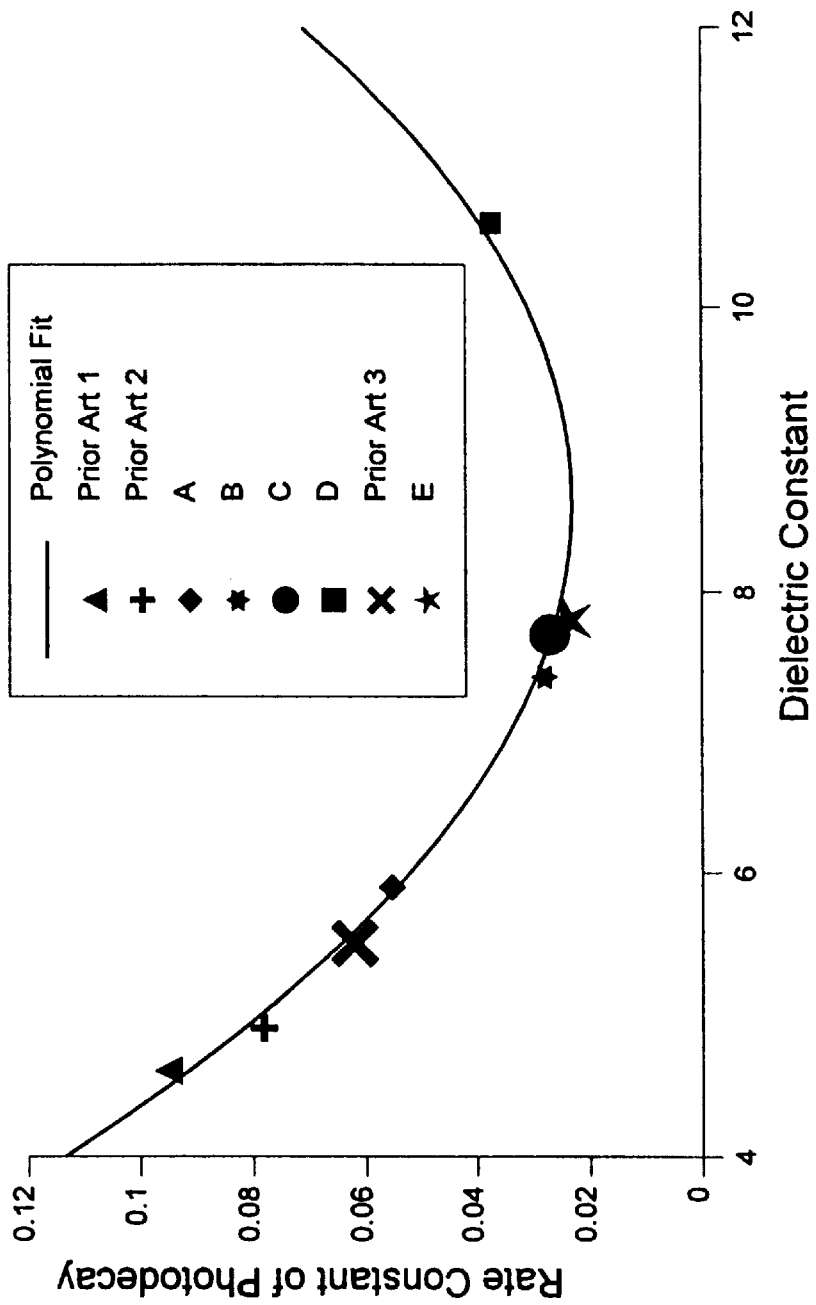
FIG. 2 is a plot of rate constant of photodecay versus dielectric constant for two additional sunscreen formulations having the same filter set as used in the data of FIG. 1, overlayed on the data of FIG. 1 and the original polynomial fit to the data of FIG. 1, for comparison.

FIG. 2 plots the rate constant of photodecay versus dielectric constant for the formulations of Table 5, overlayed on the data of FIG. 1 and the original polynomial fit to the data of FIG. 1, for comparison.

As shown in the figure, the second-order polynomial fit to the original six data points was highly predictive of the rate constant of photodecay of the two new formulations "Prior Art 3" and "E." Also, as expected based on the theory described herein, formulations C and E, which had low rate constants of photodecay (near the theoretical minimum), provided SPFs determined in independent testing that were much higher than the prior art formulation.

Example 3

A series of sunscreen compositions having a different filter system was produced according to the oil phase ingredients and concentrations (formulations) shown in Table 6 below. Parallel dielectric constant and rate constant of photodecay measurements were made according to the methods described in Example 1.

TABLE 6

|  | $\epsilon$ | Prior Art 4 | F | G | H |
| --- | --- | --- | --- | --- | --- |
|  |  | Concentrations reported as wt. % of total formulation | | | |
| octyl salicylate | 6.2 | 5% | 5% | 5% | 5% |
| avobenzone | 10* | 2% | 2% | 2% | 2% |
| saturated hydrocarbon | 2.04 to 2.13 | | | | |
| $C_{12}$–$C_{15}$ alkyl benzoates | 3.78 | 10% | | | |
| diethylhexyl malate | 5.88 | | 15% | 10% | 7.5% |
| isododecyl alcohol dimer w/HDI | 10* | | | 5% | |
| N,N-dimethyldecanamide | 12.43 | | | | 7.5% |
| oil phase dielectric constant ($\epsilon$) | | 4.43 | 6.84 | 7.33 | 10.23 |
| photodecay rate constant (% of theoretical minimum) | | 0.57 (1326%) | 0.253 (588%) | 0.186 (433%) | 0.051 (119%) |

*denotes estimated value

The formulation labeled "Prior Art 4" was formulated using typical prior art solvents, in typical concentrations. Formulations "F" to "H" were formulated according to the disclosure herein, and resulted in higher dielectric constants of the oil phases.

Figure 3:
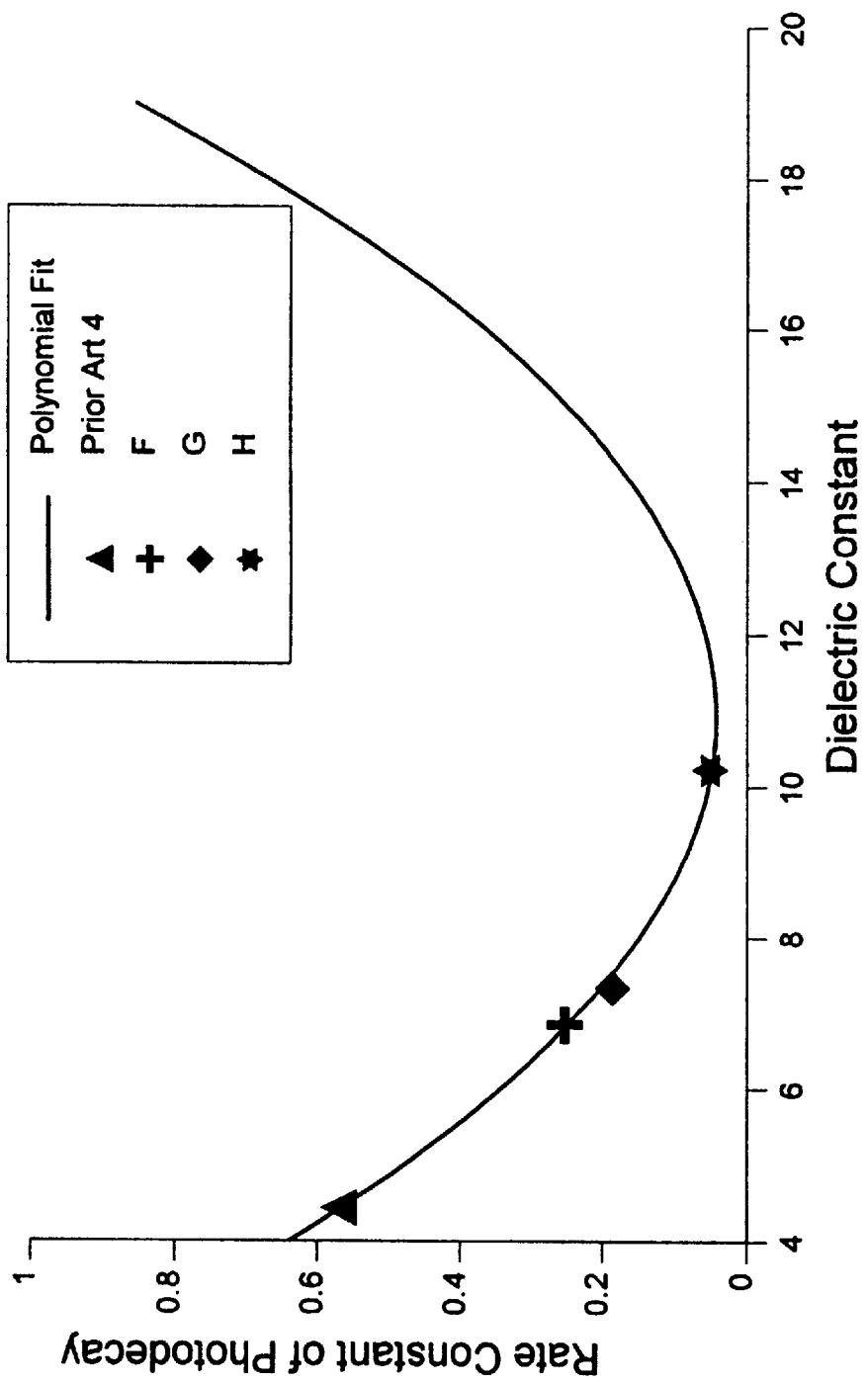
FIG. 3 is a plot of rate constant of photodecay versus dielectric constant for various sunscreen formulations having another filter set. A curve for a second-order polynomial fit to the data is displayed for comparison.

FIG. 3 plots the rate constant of photodecay versus dielectric constant for each formulation described in Table 6 above. This Figure shows that as the dielectric constant of the oil phase was increased, the rate constant of photodecay unexpectedly approached a minimum in second-order fashion.

The data were then fit to a second order polynomial having the form of general equation (ii)

$$k = -(x\epsilon^2 + y\epsilon + z) \quad \text{(ii)}$$

with the result that x=-0.01245, y=0.27179, and z=-1.52649. The polynomial provided a very good fit to the data (strong correlation), as evidenced by a coefficient of determination ($R^2$) of 0.9961. Tihus, a definite, direct relationship also exists between the polarity (dielectric constant) and the rate of photodecay of this filter system. The second-order polynomial curve is displayed on FIG. 5 for comparison. According to equation (iii) described above, the dielectric constant at the theoretical minimum rate constant of photodecay for this filter system is 10.92, and the theoretical minimum rate constant of photodecay is 0.043.

Example 4

A series of sunscreen compositions having yet another filter system was produced according to the oil phase ingredients and concentrations (formulations) shown in Table 7 below. Parallel dielectric constant and rate constant of photodecay measurements were made according to the methods redescribed in Example 1.

TABLE 7

|  | | Prior Art 5 | I | J | K |
|  | | Concentrations reported as wt. % of total formulation | | | |
|  | $\epsilon$ | | | | |
| octyl salicylate | 6.2 | 5% | 5% | 5% | 5% |
| benzophenone-3 | 13† | 3% | 3% | 3% | 3% |
| ethylhexyl methoxy-cinnamate | 5.98 | 3% | 3% | 3% | 3% |
| avobenzone | 10* | 2% | 2% | 2% | 2% |
| $C_{12}$–$C_{15}$ alkyl benzoates | 3.78 | 15% | | | |
| diethylhexyl malate | 5.88 | | 15% | | 5% |
| diisoamyl malate | 7.42 | | | 10% | |
| isododecyl alcohol dimer w/HDI | 10* | | | 5% | |
| N,N-dimethyldecanamide | 12.43 | | | | 10% |
| oil phase dielectric constant ($\epsilon$) | | 5.77 | 7.38 | 8.31 | 10.85 |
| photodecay rate constant (% of theoretical minimum) | | 0.0918 (299%) | 0.0369 (120%) | 0.0332 (108%) | 0.0835 (272%) |

*denotes estimated value
†denotes literature value

The formulation labeled "Prior Art 5" was formulated using typical prior art solvents, in typical concentrations. Formulations "I" to "K" were formulated according to the disclosure herein, and resulted in higher dielectric constants of the oil phases.

Figure 4:
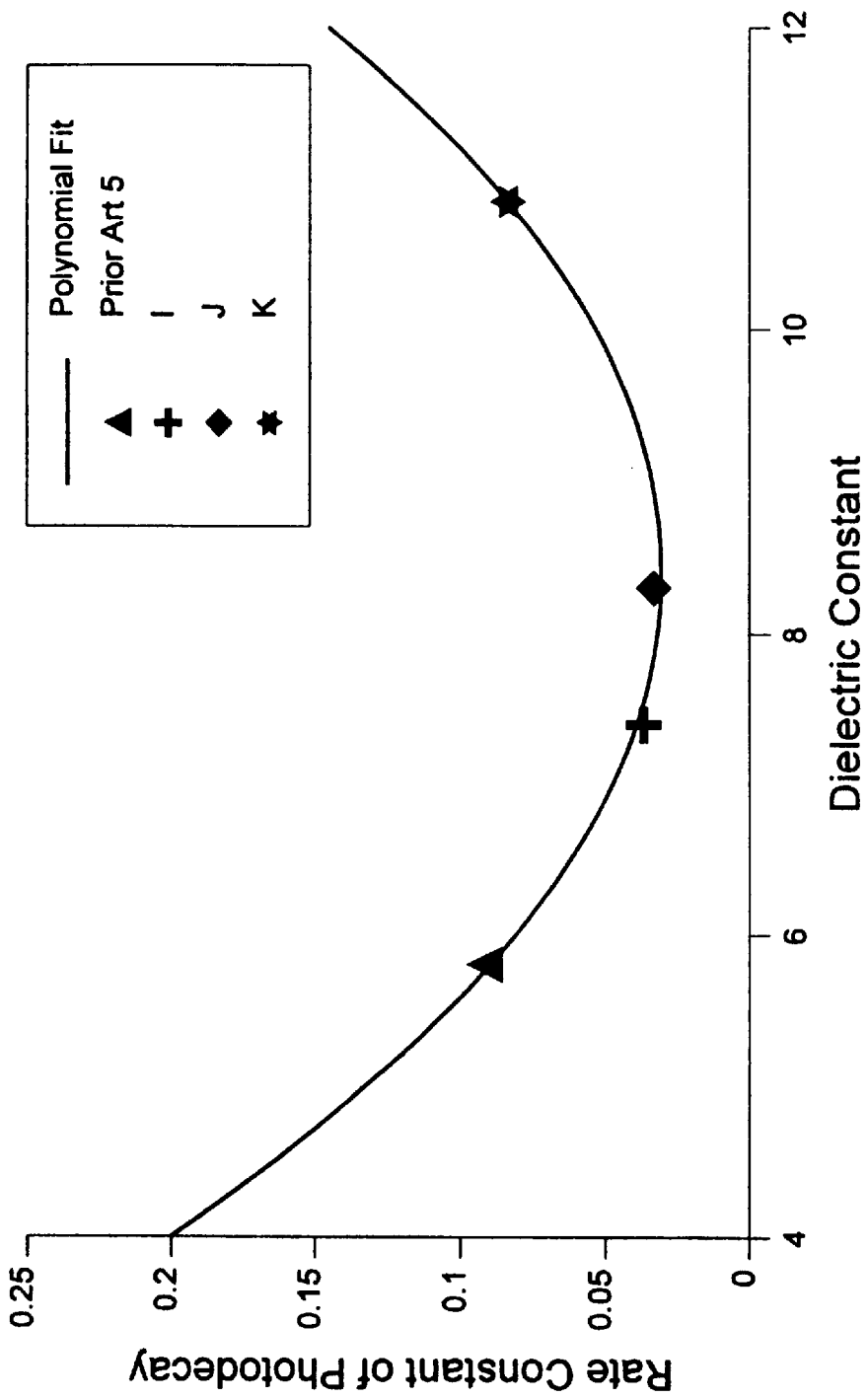
FIG. 4 is a plot of rate constant of photodecay versus dielectric constant for various sunscreen formulations having yet another filter set. A curve for a second-order polynomial fit to the data is displayed for comparison.

FIG. 4 plots the rate constant of photodecay versus dielectric constant for each formulation described in Table 5 above. This Figure shows that as the dielectric constant of the oil phase was increased, the rate constant of photodecay approached a minimum and then, quite surprisingly, increased again.

The data were then fit to a second order polynomial having the form of general equation (ii)

$$k = -(x\epsilon^2 + y\epsilon + z) \quad \text{(ii)}$$

with the result that x=−0.008795, y=0.147609, and z=−0.65001. The polynomial provided a very good fit to the data (strong correlation), as evidenced by a coefficient of determination ($R^2$) of 0.9944. Thus, a definite, direct relationship also exists between the polarity (dielectric constant) and the rate of photodecay of this filter system. The second-order polynomial curve is displayed on FIG. 6 for comparison. According to equation (iii) described above, the dielectric constant at the theoretical minimum rate constant of photodecay for this filter system is 8.39, and the theoretical minimum rate constant of photodecay is 0.0307.

Example 5

To test the predictive value of a method of formulating a sunscreen composition disclosed herein. two additional sunscreen compositions were produced using the same filter system as in Example 4, and parallel dielectric constant and rate constant of photodecay measurements were made. Subsequently, the two new formulations were sent to an independent laboratory for SPF testing of each formulation performed on five human subjects. The sunscreen compositions were produced according to the oil phase ingredients and concentrations (formulations) shown in Table 8 below. Dielectric constants and rate constants of photodecay were measured as described in Example 1, and resulted in the values reported in Table 8 below.

TABLE 8

|  | | Prior Art 6 | L |
|  | | Concentrations reported as wt. % of total formulation | |
|  | $\epsilon$ | | |
| octyl salicylate | 6.2 | 5% | 5% |
| benzophenone-3 | 13† | 3% | 3% |
| ethylhexyl methoxycinnamate | 5.98 | 3% | 3% |
| avobenzone | 10* | 2% | 2% |
| octyldodecyl neopentanoate | 3.04 | 5% | |
| $C_{12}$–$C_{15}$ alkyl benzoates | 3.78 | 10% | |
| dibutyloctyl malate | 4.65 | | 5% |
| diethylhexyl malate | 5.88 | | 10% |
| oil phase dielectric constant ($\epsilon$) | | 5.54 | 7.65 |
| photodecay rate constant | | 0.0951 | 0.03675 |
| (% of theoretical minimum) | | (310%) | (120%) |
| Average SPF | | 17.8 | 22.1 (+24%) |
| (% increase over prior art) | | | |

*denotes estimated value
†denotes literature value

The formulation labeled "Prior Art 6" was formulated using typical prior art solvents, in typical concentrations. Formulation "L" was formulated according to the disclosure herein, and resulted in higher dielectric constant of the oil phase.

Figure 5:
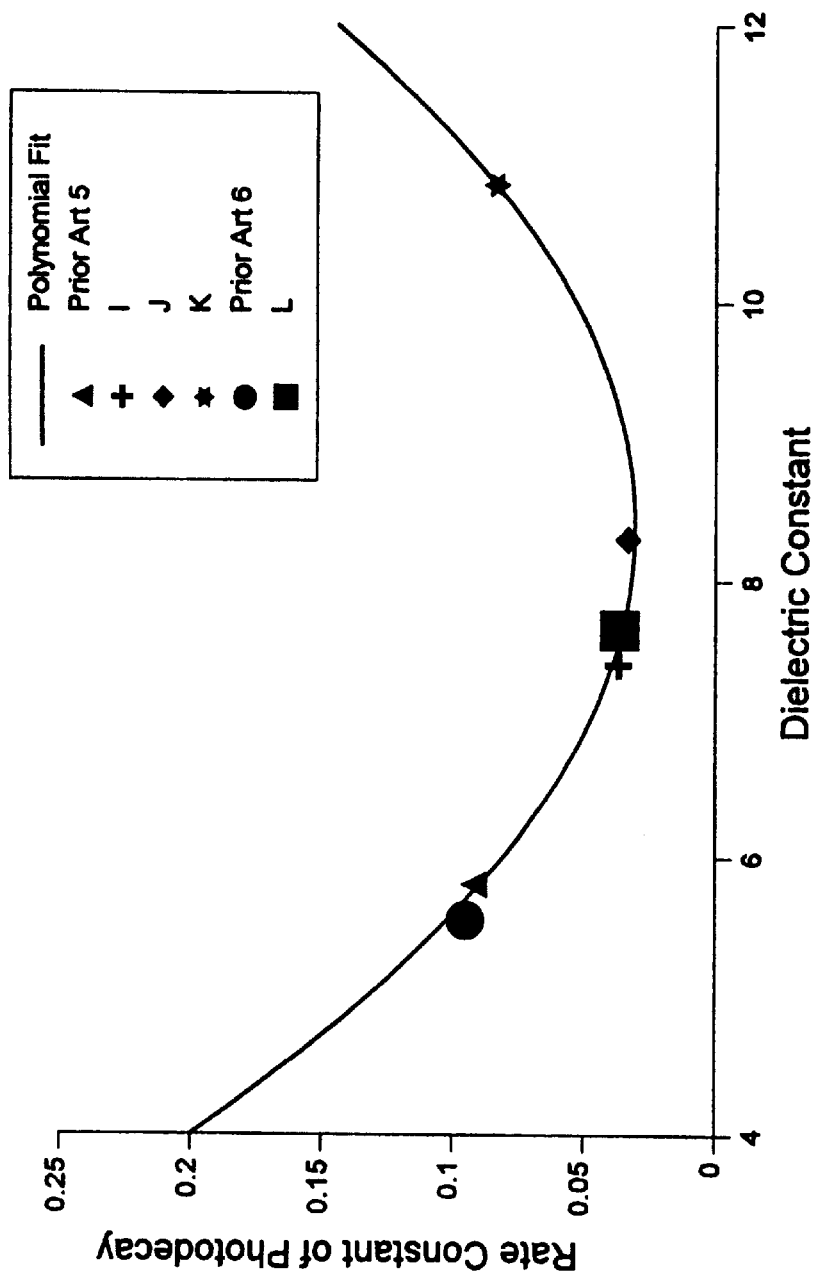
FIG. 5 is a plot of rate constant of photodecay versus dielectric constant for two additional sunscreen formulations having the same filter set as used in the data of FIG. 4, overlayed on the data of FIG. 4 and the original polynomial fit to the data of FIG. 4, for comparison.

FIG. 5 plots the rate constant of photodecay versus dielectric constant for the formulations of Table 8, overlayed on the data of FIG. 4 and the original polynomial fit to the data of FIG. 4, for comparison.

As shown in FIG. 5, the second-order polynomial fit to the original four data points was highly predictive of the rate constant of photodecay of the two new formulations "Prior Art 6" and "L." Also, as expected based on the theory described herein, formulation L, which had a relatively low rate constant of photodecay, provided an SPF determined in independent testing that was much higher than that of the prior art formulation.

Example 6

A series of sunscreen compositions having more robust filter system typical of a high SPF (e.g., 30+) sunscreen was produced according to the oil phase ingredients and concentrations (formulations) shown in Table 9 below. Parallel dielectric constant and rate constant of photodecay measurements were made according to the methods described in Example 1.

TABLE 9

|  | | Prior Art 7 | M | N |
|  | | Concentrations reported as wt. % of total formulation | | |
|  | $\epsilon$ | | | |
| octyl salicylate | 6.2 | 5% | 5% | 5% |
| benzophenone-3 | 13† | 4% | 4% | 4% |
| ethylhexyl methoxycinnamate | 5.98 | 6% | 6% | 6% |
| avobenzone | 10* | 3% | 3% | 3% |

TABLE 9-continued

|  | ϵ | Prior Art 7 M N Concentrations reported as wt. % of total formulation | | |
|---|---|---|---|---|
| $C_{12}$–$C_{15}$ alkyl benzoates | 3.78 | 8% | | |
| diethylhexyl malate | 5.88 | | 8% | 3% |
| N,N-dimethyldecanamide | 12.43 | | | 5% |
| oil phase dielectric constant (ϵ) | | 6.91 | 7.95 | 10.25 |
| photodecay rate constant | | 0.0278 | 0.0177 | 0.0365 |
| (% of theoretical minimum) | | (164%) | (105%) | (216%) |

*denotes estimated value
†denotes literature value

The formulation labeled "Prior Art 7" was formulated using a typical prior art solvent, in a typical concentration. Formulations "M" and "N" were formulated according to the disclosure herein, and resulted in higher dielectric constants of the oil phases.

Figure 6:
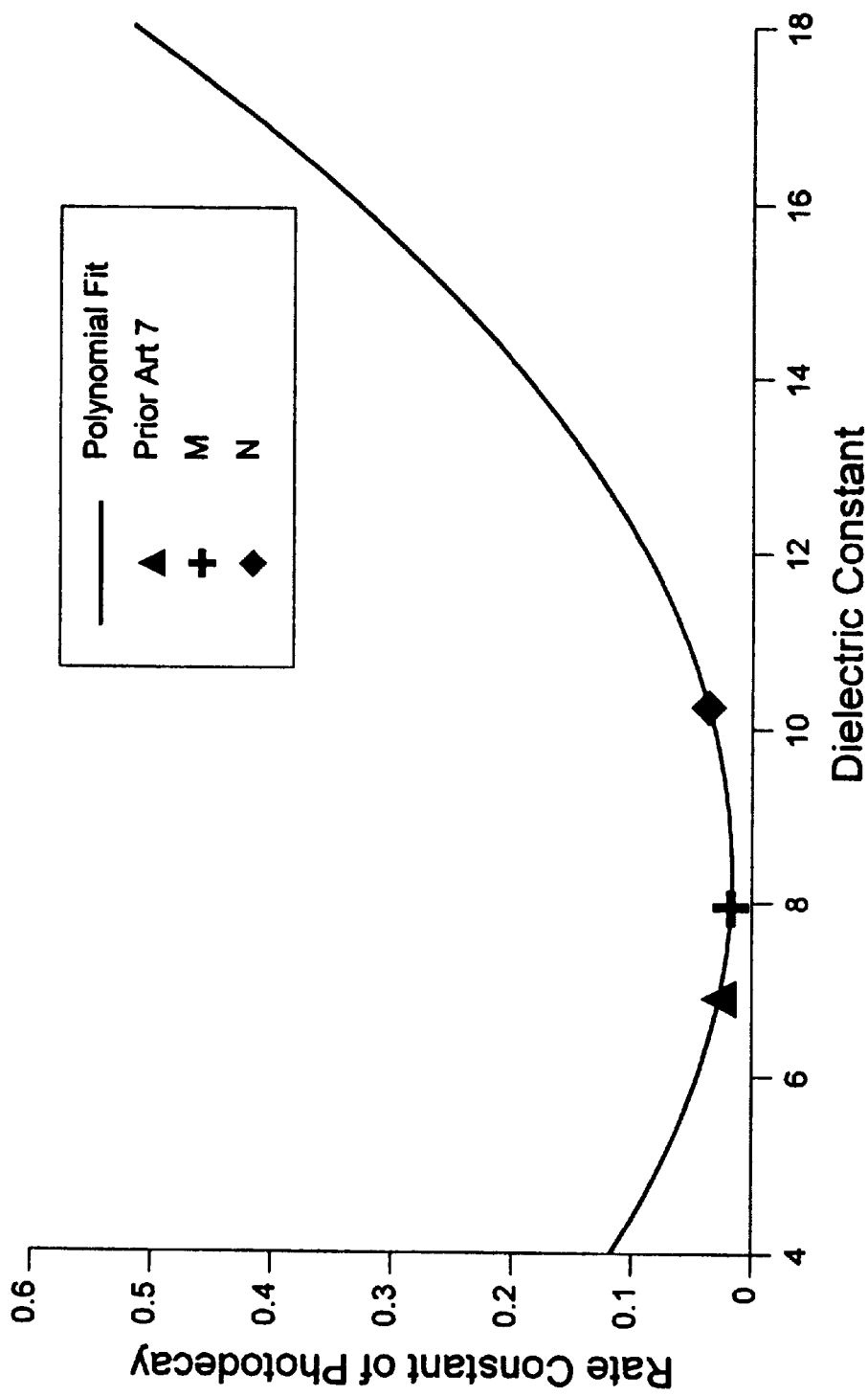
FIG. 6 is a plot of rate constant of photodecay versus dielectric constant for various sunscreen formulations having still another filter set. A curve for a second-order polynomial fit to the data is displayed for comparison.

FIG. 6 plots the rate constant of photodecay versus dielectric constant for each formulation described in Table 9 above. This Figure shows that as the dielectric constant of the oil phase was increased, the rate constant of photodecay approached a minimum and then, quite surprisingly, increased again.

The data were then fit to a second order polynomial having the form of general equation (ii)

$$k = -(x\epsilon^2 + y\epsilon + z) \quad (ii)$$

with the result that x=−0.005355, y=0.089286, and z=−0.38908. The polynomial provided a very good fit to the data (strong correlation), as evidenced by a coefficient of determination ($R^2$) of 1. Thus, a definite, direct relationship also exists between the polarity (dielectric constant) and the rate of photodecay of this filter system. The second-order polynomial curve is displayed on FIG. 6 for comparison. According to equation (iii) described above, the dielectric constant at the theoretical minimum rate constant of photodecay for this filter system is 8.34, and the theoretical minimum rate constant of photodecay is 0.0169.

One or more advantages becomes possible by practice of a method disclosed herein or by use of a composition described herein. For example, financial savings can be achieved by practice of one method described herein to formulate a new cosmetically-acceptable sunscreen composition having the same SPF as a prior art composition but using a lower concentration of expensive UV filters. Alternatively, a high-SPF cosmetic sunscreen composition can be formulated within government-mandated limits on the use of particular UV filters, by choosing a solvent or solvent blend disclosed herein. As another example, a known sunscreen formulation can be modified to be more photostable and, thus, have a higher SPF, by simply adding or substituting a highly polar solvent, such as those described herein, for a solvent in the sunscreen formulation that has a relatively low polarity. By practice of a method described herein, valuable time and resources can be saved by formulating a sunscreen to have a desired SPF. without the use of trial-and-error experimentation. Further aspects and advantages of the invention will become apparent to those of ordinary skill in the art in view of the disclosure herein.

The foregoing description is given for clearness of understanding only, and no unnecessary limitations should be understood therefrom, as modifications within the scope of the invention may be apparent to those having ordinary skill in the art.

What is claimed is:

1. A method of preparing a sunscreen comprising a solvent system and a filter system, said method comprising the step of:

controlling the polarity of said solvent system to control the rate of photodecay of the filter system.

2. The method of claim 1, comprising controlling the polarity of said solvent system to minimize the rate of photodecay of the filter system.

3. The method of claim 2, comprising controlling the dielectric constant of said solvent system to minimize the rate of photodecay of the filter system.

4. A method of formulating a sunscreen composition, comprising the steps of:

selecting a filter system comprising a photoactive compound;

selecting a plurality of analytical solvent systems for the filter system, each analytical solvent system comprising a lipophilic organic compound;

preparing parallel mixtures of said filter system in said plurality of analytical solvent systems, all of the mixtures having substantially the same concentration of filter system;

determining the polarity of each of said mixtures;

determining a rate constant of photodecay of each of said mixtures at a selected wavelength;

selecting a final solvent system based on the polarity of said final solvent system; and mixing said filter system and said final solvent system.

5. The method of claim 4, further comprising the step of preparing an emulsion from an aqueous system and said mixture of said filter system and said solvent system.

6. The method of claim 5, wherein said emulsion is an oil-in-water emulsion.

7. The method of claim 4, wherein the filter system comprises a dibenzoylmethane derivative.

8. The method of claim 7, wherein the dibenzoylmethane derivative comprises avobenzone.

9. The method of claim 4, wherein the filter system comprises a paramethoxycinnamic acid ester.

10. The method of claim 4, wherein said plurality of analytical solvent systems is selected based on the polarity of each solvent system.

11. The method of claim 10, wherein said plurality of analytical solvent systems are selected to provide mixtures with said filter system having a range of polarities.

12. The method of claim 10, wherein said plurality of analytical solvent systems is selected based on the dielectric constant of each solvent system.

13. The method of claim 12, wherein said plurality of analytical solvent systems are selected to provide mixtures with said filter system having a range of dielectric constants.

14. The method of claim 4, wherein an analytical solvent system comprises a compound selected from the group consisting of an amide, a bis-urethane, a malate, and mixtures thereof.

* * * * *

UNITED STATES PATENT AND TRADEMARK OFFICE
CERTIFICATE OF CORRECTION

PATENT NO.    : 6,537,529 B1
DATED         : March 25, 2003
INVENTOR(S)   : Craig A. Bonda It is certified that error appears in the above-identified patent and that said Letters Patent is hereby corrected as shown below:

<u>Column 6,</u>
Lines 5-63, delete claims 1-14 and substitute therefore claims 1-52.

1. A method of preparing a sunscreen comprising a solvent system and a filter system, said method comprising the step of:
 controlling the polarity of said solvent system to control the rate of photodecay of the filter system.

2. The method of claim 1, comprising controlling the polarity of said solvent system to minimize the rate of photodecay of the filter system.

3. The method of claim 2, comprising controlling the dielectric constant of said solvent system to minimize the rate of photodecay of the filter system.

4. A method of formulating a sunscreen composition, comprising the steps of:

selecting a filter system comprising a photoactive compound;
 selecting a plurality of analytical solvent systems for the filter system, each analytical solvent system comprising a lipophilic organic compound;
 preparing parallel mixtures of said filter system in said plurality of analytical solvent systems, all of the mixtures having substantially the same concentration of filter system;
 determining the polarity of each of said mixtures;
 determining a rate constant of photodecay of each of said mixtures at a selected wavelength;
 selecting a final solvent system based on the polarity of said final solvent system; and
 mixing said filter system and said final solvent system.

5. The method of claim 4, further comprising the step of preparing an emulsion from an aqueous system and said mixture of said filter system and said solvent system.

6. The method of claim 5, wherein said emulsion is an oil-in-water emulsion.

7. The method of claim 4, wherein the filter system comprises a dibenzoylmethane derivative.

8. The method of claim 7, wherein the dibenzoylmethane derivative comprises avobenzone.

9. The method of claim 4, wherein the filter system comprises a paramethoxycinnamic acid ester.

UNITED STATES PATENT AND TRADEMARK OFFICE
CERTIFICATE OF CORRECTION

PATENT NO. : 6,537,529 B1　　　　　　　　　　　　　　　　　　　　Page 2 of 5
DATED : March 25, 2003
INVENTOR(S) : Craig A. Bonda It is certified that error appears in the above-identified patent and that said Letters Patent is hereby corrected as shown below:

<u>Column 6 cont'd,</u>

10.　The method of claim 4, wherein said plurality of analytical solvent systems is selected based on the polarity of each solvent system.

11.　The method of claim 10, wherein said plurality of analytical solvent systems are selected to provide mixtures with said filter system having a range of polarities.

12.　The method of claim 10, wherein said plurality of analytical solvent systems is selected based on the dielectric constant of each solvent system.

13.　The method of claim 12, wherein said plurality of analytical solvent systems are selected to provide mixtures with said filter system having a range of dielectric constants.

14.　The method of claim 4, wherein an analytical solvent system comprises a compound selected from the group consisting of an amide, a bis-urethane, a malate, and mixtures thereof.

15.　The method of claim 14, wherein an analytical solvent system comprises an amide.

16.　The method of claim 14, wherein an analytical solvent system comprises a bis-urethane.

17.　The method of claim 14, wherein an analytical solvent system comprises a malate.

18.　The method of claim 4, wherein determining the polarity of each of said mixtures comprises determining the dielectric constant of each of said mixtures.

19.　The method of claim 4, wherein determining a polarity comprises measuring a property that is a function of polarity.

20.　The method of claim 19, wherein determining a polarity comprises measuring a dielectric constant.

21.　The method of claim 4, wherein determining a polarity comprises retrieving a value of a property that is a function of polarity from a reference document.

22.　The method of claim 21, wherein determining a polarity comprises retrieving a dielectric constant value from a reference document.

UNITED STATES PATENT AND TRADEMARK OFFICE
CERTIFICATE OF CORRECTION

PATENT NO. : 6,537,529 B1
DATED : March 25, 2003
INVENTOR(S) : Craig A. Bonda

It is certified that error appears in the above-identified patent and that said Letters Patent is hereby corrected as shown below:

Column 6 cont'd,

23. The method of claim 4, wherein determining a rate constant of photodecay of a mixture at a selected wavelength comprises
measuring absorbance of the mixture at said wavelength before irradiation and after each of a plurality of exposures to radiation at said wavelength;
and calculating said rate constant based on said measurements.

24. The method of claim 4, wherein determining a rate constant of photodecay of a mixture at a selected wavelength comprises retrieving the rate constant of photodecay from a reference document.

25. The method of claim 4, wherein selecting a final solvent system based on the polarity of said final solvent system comprises selecting a final solvent system based on the dielectric constant of said final solvent system.

26. The method of claim 4, wherein selecting a final solvent system based on the polarity of said final solvent system comprises selecting a final solvent system that has a polarity that is at least about 80% of the polarity at the theoretical minimum rate constant of photodecay for the filter system.

27. The method of claim 26, wherein selecting a final solvent system based on the polarity of said final solvent system comprises selecting a final solvent system that has a dielectric constant that is at least about 80% of the dielectric constant at the theoretical minimum rate constant of photodecay for the filter system.

28. The method of claim 27, wherein selecting a final solvent system based on the polarity of said final solvent system comprises selecting a final solvent system that has a dielectric constant that is about 80% to about 120% of the dielectric constant at the theoretical minimum rate constant of photodecay for the filter system.

29. A method of formulating an emulsion sunscreen composition, comprising the steps of:

selecting a filter system comprising a photoactive compound;
selecting a plurality of analytical solvent systems for the filter system, each analytical solvent system comprising a lipophilic organic compound;
preparing parallel mixtures of said filter system in said plurality of analytical solvent systems, all of the mixtures having substantially the same concentration of filter system;
determining the polarity of each of said mixtures;
selecting an aqueous system;

preparing parallel emulsions from said aqueous system and said mixtures;
determining the rate constant of photodecay of each of said emulsions;
selecting a final solvent system based on the polarity of said final solvent system; and
preparing an emulsion from said final solvent system, said filter system, and said aqueous system.

30. The method of claim 29, wherein said emulsion is an oil-in-water emulsion.

UNITED STATES PATENT AND TRADEMARK OFFICE
CERTIFICATE OF CORRECTION

| | |
|---|---|
| PATENT NO. : 6,537,529 B1 | |
| DATED : March 25, 2003 | |
| INVENTOR(S) : Craig A. Bonda | |

It is certified that error appears in the above-identified patent and that said Letters Patent is hereby corrected as shown below:

Column 6 cont'd,

31. The method of claim 29, wherein the filter system comprises a dibenzoylmethane derivative.

32. The method of claim 31, wherein the dibenzoylmethane derivative comprises avobenzone.

33. The method of claim 29, wherein the filter system comprises a paramethoxycinnamic acid ester.

34. The method of claim 29, wherein said plurality of analytical solvent systems is selected based on the polarity of each solvent system.

35. The method of claim 34, wherein said plurality of analytical solvent systems are selected to provide mixtures with said filter system having a range of polarities.

36. The method of claim 34, wherein said plurality of analytical solvent systems is selected based on the dielectric constant of each solvent system.

37. The method of claim 36, wherein said plurality of analytical solvent systems are selected to provide mixtures with said filter system having a range of dielectric constants.

38. The method of claim 29, wherein an analytical solvent system comprises a compound selected from the group consisting of an amide, a bis-urethane, a malate, and mixtures thereof.

39. The method of claim 38, wherein an analytical solvent system comprises an amide.

40. The method of claim 38, wherein an analytical solvent system comprises a bis-urethane.

41. The method of claim 38, wherein an analytical solvent system comprises a malate.

42. The method of claim 29, wherein determining the polarity of each of said mixtures comprises determining the dielectric constant of each of said mixtures.

43. The method of claim 29, wherein determining a polarity comprises measuring a property that is a function of polarity.

44. The method of claim 43, wherein determining a polarity comprises measuring a dielectric constant.

45. The method of claim 29, wherein determining a polarity comprises retrieving a value of a property that is a function of polarity from a reference document.

46. The method of claim 45, wherein determining a polarity comprises retrieving a dielectric constant value from a reference document.

UNITED STATES PATENT AND TRADEMARK OFFICE
CERTIFICATE OF CORRECTION

PATENT NO.     : 6,537,529 B1
DATED          : March 25, 2003
INVENTOR(S)    : Craig A. Bonda It is certified that error appears in the above-identified patent and that said Letters Patent is hereby corrected as shown below:

<u>Column 6 cont'd,</u>

47. The method of claim 29, wherein determining a rate constant of photodecay of an emulsion at a selected wavelength comprises
measuring absorbance of the emulsion at said wavelength before irradiation and after each of a plurality of exposures to radiation at said wavelength;
and calculating said rate constant based on said measurements.

48. The method of claim 29, wherein determining a rate constant of photodecay of an emulsion at a selected wavelength comprises retrieving the rate constant of photodecay from a reference document.

49. The method of claim 29, wherein selecting a final solvent system based on the polarity of said final solvent system comprises selecting a final solvent system based on the dielectric constant of said final solvent system.

50. The method of claim 29, wherein selecting a final solvent system based on the polarity of said final solvent system comprises selecting a final solvent system that has a polarity that is at least about 80% of the polarity at the theoretical minimum rate constant of photodecay for the filter system.

51. The method of claim 50, wherein selecting a final solvent system based on the polarity of said final solvent system comprises selecting a final solvent system that has a dielectric constant that is at least about 80% of the dielectric constant at the theoretical minimum rate constant of photodecay for the filter system.

52. The method of claim 51, wherein selecting a final solvent system based on the polarity of said final solvent system comprises selecting a final solvent system that has a dielectric constant that is about 80% to about 120% of the dielectric constant at the theoretical minimum rate constant of photodecay for the filter system.

Signed and Sealed this

Nineteenth Day of August, 2003

JAMES E. ROGAN
*Director of the United States Patent and Trademark Office*